United States Patent
Hari et al.

(10) Patent No.: US 9,718,896 B2
(45) Date of Patent: Aug. 1, 2017

(54) CONTROLLING A POLYOLEFIN REACTION

(71) Applicant: Univation Technologies, LLC, Houston, TX (US)

(72) Inventors: Abarajith S. Hari, Ridgecrest, CA (US); Bruce J. Savatsky, Kingwood, TX (US); David M. Glowczwski, Baytown, TX (US); Xianyi Cao, Pearland, TX (US)

(73) Assignee: Univation Technologies, LLC, Houston, TX (US)

( * ) Notice: Subject to any disclaimer, the term of this patent is extended or adjusted under 35 U.S.C. 154(b) by 114 days.

(21) Appl. No.: 14/424,819

(22) PCT Filed: Sep. 4, 2013

(86) PCT No.: PCT/US2013/057998
§ 371 (c)(1),
(2) Date: Feb. 27, 2015

(87) PCT Pub. No.: WO2014/039519
PCT Pub. Date: Mar. 13, 2014

(65) Prior Publication Data
US 2015/0210782 A1    Jul. 30, 2015

Related U.S. Application Data

(60) Provisional application No. 61/698,278, filed on Sep. 7, 2012.

(51) Int. Cl.
*C08F 2/00* (2006.01)
*C08F 2/34* (2006.01)
(Continued)

(52) U.S. Cl.
CPC .................. *C08F 2/00* (2013.01); *C08F 2/34* (2013.01); *G06F 19/702* (2013.01); *C08F 2400/02* (2013.01)

(58) Field of Classification Search
CPC ........ C08F 2/34; C08F 10/00; C08F 2400/02; G06F 19/702
(Continued)

(56) References Cited

U.S. PATENT DOCUMENTS

| 4,543,399 A | 9/1985 | Jenkins, III et al. |
| 4,588,790 A | 5/1986 | Jenkins, III et al. |

(Continued)

FOREIGN PATENT DOCUMENTS

| WO | WO 03/051929 | 6/2003 |
| WO | WO 2005/049663 | 6/2005 |

(Continued)

OTHER PUBLICATIONS

"Acoustic Emission Technology—a New Sensing Technique for Optimising Polyolefin Production" (2000).
(Continued)

*Primary Examiner* — Fred M Teskin
(74) *Attorney, Agent, or Firm* — Brooks, Cameron & Huebsch, PLLC

(57) ABSTRACT

Methods and systems for controlling a polymerization reaction in a non-sticking regime are disclosed. An exemplary method includes measuring parameters for the polymerization reaction including a reactor temperature and a concentration of an induced condensing agent (ICA) in a polymerization reactor. An equivalent partial pressure (($P_{ICA})_{equiv}$) of the ICA is calculated. The polymerization reaction is located in a two dimension space defined by a reactor temperature dimension and a (($P_{ICA})_{equiv}$) dimension. The location in the two dimensional space is compared to an non-sticking regime, defined as the space between an upper temperature limit (UTL) curve and a lower temperature limit
(Continued)

(LTL) curve. The parameters of the polymerization reaction are adjusted to keep the polymerization reaction within the non-sticking regime.

19 Claims, 21 Drawing Sheets

(51) Int. Cl.
*C08F 10/00* (2006.01)
*G06F 19/00* (2011.01)
*C08F 210/16* (2006.01)

(58) Field of Classification Search
USPC .......................................... 526/61; 700/269
See application file for complete search history.

(56) References Cited

U.S. PATENT DOCUMENTS

| | | |
|---|---|---|
| 5,352,749 A | 10/1994 | DeChellis et al. |
| 5,405,922 A | 4/1995 | DeChellis et al. |
| 5,436,304 A | 7/1995 | Griffin et al. |
| 7,774,178 B2 * | 8/2010 | Pannell .................. C08F 10/00 526/59 |
| 2004/0063871 A1 | 4/2004 | Parrish et al. |
| 2005/0267269 A1 | 12/2005 | Hagerty et al. |
| 2007/0060721 A1 | 3/2007 | Muhle et al. |
| 2007/0073010 A1 | 3/2007 | Pannell et al. |
| 2009/0234081 A1 | 9/2009 | Thomas, Jr. et al. |
| 2010/0286346 A1 | 11/2010 | Muhle et al. |

FOREIGN PATENT DOCUMENTS

| | | |
|---|---|---|
| WO | WO 2005/113615 A2 | 12/2005 |
| WO | WO 2006/009980 | 1/2006 |
| WO | WO 2008/030294 A1 | 3/2008 |
| WO | WO 2008/100368 | 8/2008 |

OTHER PUBLICATIONS

"Agglomeration Detection by Acoustic Emission," PAA Application note: 2002/111 (2000).

Arden et al., "Model Prediction for Reactor Control," Chemical Engineering Progress, American Inst. of Chem. Eng., US, vol. 79, No. 6, (Jun. 1983).

* cited by examiner

500

1300

1400

1500

1800

CONTROLLING A POLYOLEFIN REACTION

CROSS-REFERENCE TO RELATED APPLICATIONS

This application is a National Stage application under 35 U.S.C. §371 of International Application No. PCT/US2013/57998, filed Sep. 4, 2013, that claims the benefit of Ser. No. 61/698,278, filed Sep. 7, 2012, the disclosures of which are incorporated by reference in their entireties.

FIELD OF THE INVENTION

Described herein are systems and methods for controlling a polyolefin polymerization reaction. The methods may include determining a non-sticking operating regime for a polyolefin polymerization reaction to prevent the materials in the reaction from agglomerating and operating a polyolefin polymerization reaction within the non-sticking operating regime.

BACKGROUND

Polyolefin polymers can be produced using gas phase polymerization processes. In a typical gas-phase fluidized bed polymerization process, a gaseous stream containing one or more monomers is continuously passed through the fluidized bed under reactive conditions in the presence of a catalyst. The gaseous stream is withdrawn from the fluidized bed and recycled back into the reactor. The recycled gas stream is heated in the reactor by the heat of polymerization. This heat may be removed in another part of the cycle, for example by a cooling system external to the reactor such as a heat exchanger.

The heat generated by the reaction may be removed in order to maintain the temperature of the resin and gaseous stream inside the reactor below the polymer melting point or the catalyst deactivation temperature, or to control polymer properties. Heat removal can also help prevent excessive stickiness of polymer particles that may result in agglomeration. Particle agglomerations may lead to the formation of chunks or sheets of polymer that cannot be removed from the reactor as product. Further, such chunks or sheets may fall onto the reactor distributor plate which may impair fluidization of the bed and may lead to a discontinuity event. Additionally, since the polymerization reaction is exothermic, the amount of polymer produced in a fluidized bed polymerization process is related to the amount of heat that can be withdrawn from the reaction zone.

For a time, it was thought that the temperature of the gaseous stream external to the reactor, otherwise known as the recycle stream temperature, could not be decreased below the dew point of the recycle stream without causing problems such as polymer agglomeration or plugging of the reactor system. The dew point of the recycle stream is that temperature at which liquid condensate first begins to form in the gaseous recycle stream. The dew point can be calculated knowing the gas composition and is thermodynamically defined using an equation of state. However, as described in U.S. Pat. Nos. 4,543,399 and 4,588,790, it was found that a recycle stream can be cooled to a temperature below the dew point in a fluidized bed polymerization process resulting in condensing a portion of the recycle gas stream outside of the reactor. The resulting stream containing entrained liquid can then be returned to the reactor without causing agglomeration or plugging phenomena. The process of purposefully condensing a portion of the recycle stream is known in the industry as "condensed mode" operation. When a recycle stream temperature is lowered to a point below its dew point in condensed mode operation, an increase in polymer production may be possible.

Cooling of the recycle stream to a temperature below the gas dew point temperature produces a two-phase gas/liquid mixture that may have entrained solids contained in both phases. The liquid phase of this two-phase gas/liquid mixture in condensed mode operation is generally entrained in the gas phase of the mixture. Vaporization of the liquid occurs only when heat is added or pressure is reduced. For example, as described in U.S. Pat. Nos. 4,543,399 and 4,588,790, vaporization can occur when the two-phase mixture enters the fluidized bed, with the resin providing the required heat of vaporization. The vaporization thus provides an additional means of extracting heat of reaction from the fluidized bed.

The cooling capacity of the recycle gas can be increased further while at a given reaction temperature and a given temperature of the cooling heat transfer medium. This can be performed by adding non-polymerizing, non-reactive materials to the reactor, which are condensable at the temperatures encountered in the process heat exchanger. Such are collectively known as induced condensing agents (ICAs). Increasing concentrations of ICA in the reactor causes corresponding increases in the dew point temperature of the reactor gas, which promotes higher levels of condensing for higher (heat transfer limited) production rates from the reactor. Suitable ICAs are selected based on their specific heat and boiling point properties. In particular, an ICA is selected such that a relatively high portion of the material is condensed at the cooling water temperatures available in polymer production plants, which are compounds typically having a boiling point of about 20-40° C. ICAs include hexane, isohexane, pentane, isopentane, butane, isobutane, and other hydrocarbon compounds that are similarly non-reactive in the polymerization process.

U.S. Pat. No. 5,352,749, describes limits to the concentrations of condensable gases, whether ICAs, comonomers or combinations thereof, that can be tolerated in the reaction system. Above certain limiting concentrations, the condensable gases can cause a sudden loss of fluidization in the reactor, and a consequent loss in ability to control the temperature in the fluid bed. The upper limits of ICA in the reactor may depend on the type of polymer being produced. For example U.S. Pat. Nos. 5,352,749, 5,405,922, and 5,436,304, characterize this limit by tracking the ratio of fluidized bulk density to settled bulk density. As the concentration of isopentane was increased, they found that the bulk density ratio steadily decreased. When the concentration of isopentane was sufficiently high, corresponding to a bulk density ratio of 0.59, they found that fluidization in the reactor was lost. They therefore determined that this ratio (0.59) was a point of no return, below which the reactor will cease functioning due to loss of fluidization. As described in PCT Publication WO 2005/113615(A2), attempts to operate polymerization reactors with excessive ICA concentrations may cause polymer particles suspended in the fluid bed to become cohesive or "sticky," and in some cases cause the fluid bed to solidify in the form of a large chunk.

Adding to the complexity of control of stickiness while using ICAs, different polymer products vary widely in their ability to tolerate ICA materials, some having a relatively high tolerance (expressed in partial pressure of the ICA in the reactor), e.g., 50 psia, while other polymers may tolerate as little as 5 psia. In these latter polymers, the heat transfer limited production rates under similar conditions are substantially lower. Polymers which possess a more uniform comonomer composition distribution are known to have a higher tolerance to the partial pressure of the ICA in the reactor. Typical metallocene catalysts are a good example of catalysts that may produce polymers having a more uniform comonomer composition. However, at some point even these metallocene produced polymers reach a limiting ICA concentration that induces stickiness. The limiting ICA concentration depends on several factors in addition to the polymer type, including reactor temperature, comonomer type, and concentration. Further, with the effect of temperature, ICA level, and comonomer levels all affecting on the onset of stickiness, determining the point at which sticking begins to occur has heretofore been difficult.

Two articles by Process Analysis & Automation Limited (PAA), entitled "Agglomeration Detection by Acoustic Emission," PAA Application note: 2002/111 (2000) and "Acoustic Emission Technology—a New Sensing Technique for Optimising Polyolefin Production" (2000), suggest process control in fluidized bed production of polyolefins may be performed by utilizing acoustic emission sensors located at various positions on the reactor and recycle piping. These publications purport to solve the problem of detecting large polymer agglomerates in a reactor, such as chunks or sheets, rather than detecting stickiness of the resin particles, and provide only one specific example, showing the detection of a chunk of approximately 1.5 meters in diameter within a commercial fluid bed reactor. There is no mention of the detection of polymer stickiness or cohesiveness. In effect, the PAA documents describe the detection of agglomerates after they have been formed in the reactor, rather than detection of resin stickiness that, if left unchecked, could lead to the formation of the agglomerates.

PCT Application Publication Number WO 2003/051929 describes the use of mathematical chaos theory to detect the onset and presence of sheeting in a fluid bed reactor. However, like the PAA articles, the reference does not disclose how to predict when a resin in a reactor is going to become sticky, or any method allowing safe operation of a polymerization reactor near its limit of ultimate cooling capacity for maximum production rates.

WO 2005/113615 and corresponding U.S. Patent Application Publication No. 2005/0267269 describe determination in a laboratory of a critical temperature below which resin in a polymerization reactor cannot become sticky, and use of this predetermined critical temperature to control the reactor.

U.S. patent application Ser. No. 11/227,710 discloses monitoring of resin stickiness during operation of a polymerization reactor by generating a time series of readings of acoustic emissions of the contents of the reactor during steady state operation. Additional acoustic emission measurements are then generated and processed to determine whether they deviate from acoustic emissions indicative of steady state reactor operation. Such deviation is treated as an indication of onset of excessive stickiness of polymer particles in the reactor. Corrective action can be taken (e.g., ICA and/or monomer levels and/or reactor temperature can be adjusted) when the acoustic emission measurements are determined to deviate from those of a steady state reactor. However, this application does not teach the generation of a reference temperature above which resin in a reactor is predicted to become sticky.

Other background references include U.S. Patent Application Publication Nos. 2004/063871, 2005/0267269; 2007/073010, and WO 2005/049663, and WO 2006/009980; and "Model Prediction for Reactor Control," Ardell et al., *Chemical Engineering Progress*, American Inst. Of Chem. Eng., US, vol. 79, no. 6, (June 1983).

Even within the constraints of conventional operations, control of reactors is complex, adding further to the difficulty of finding operating conditions that may result in higher production rates. It would be desirable to provide a method of determining a stable operating condition for gas fluidized bed polymerization, especially if operating in condensed mode, to facilitate optimum design of the plant and the determination of desirable process conditions for optimum or maximum production rates in a given plant design. It would also be desirable to have a mechanism in commercial gas-phase reactors to detect the onset of stickiness that is a better or earlier indicator of the onset of stickiness than are conventional techniques (e.g., monitoring the fluidized bulk density as described in U.S. Pat. No. 5,352,749). Such a mechanism would allow the operators to determine when conditions of limiting stickiness are being approached, and enable them to take corrective action before discontinuity events occur, while keeping the reactors at or near conditions of maximum ICA concentration, permitting higher production rates with substantially less risk.

SUMMARY

An embodiment described herein provides a method for determining a stickiness temperature in a resin. The method includes adding the resin to a testing device comprising an agitator. A vacuum may be pulled on the testing device and an induced condensing agent (ICA) is added to the testing device. The agitator is run and the temperature is increased until a value of a torque used to run the agitator exceeds a limit.

Another embodiment provides a method for modeling a stickiness temperature for a resin. The method includes measuring a stickiness temperature of a resin at each of a plurality of concentrations of induced condensing agent (ICA) in a testing device. The density, melt index (MI), and high load melt index (HLMI) are measured for the resin. A melt flow ratio (MFR) is calculated by dividing the HLMI by the MI. An equivalent partial pressure of the ICA is calculated by accounting for the partial pressure of isomers that accumulate in a reactor. An equation is determined that relates the stickiness temperature to the equivalent partial pressure of the ICA, based, at least in part, on the density, the MI, and the MFR of the resin. The equation may be determined using a least squares analysis.

Another embodiment provides a method of controlling a polymerization reaction to remain in a non-sticking regime. The method includes measuring parameters for the polymerization reaction including a reactor temperature and a concentration of an induced condensing agent (ICA) in a polymerization reactor. An equivalent partial pressure $((P_{ICA})_{equiv})$ of the ICA is calculated. The polymerization reaction is located in a two dimension space defined by a reactor temperature dimension and a $((P_{ICA})_{equiv})$ dimension. The location in the two dimensional space is compared to an non-sticking regime, defined as the space between an upper temperature limit (UTL) curve and a lower temperature limit (LTL) curve. The parameters of the polymerization reaction are adjusted to keep the polymerization reaction within the non-sticking regime.

Another embodiment provides a system for controlling a reactor. The system comprises a polymerization reactor including a gas chromatograph, a temperature measurement system, and a control system. The control system includes a processor and a storage system, wherein the storage system includes machine readable instructions. The machine readable instructions are configured to direct the processor to measure a temperature of the polymerization reactor using the temperature measurement system, measure a concentration of an induced condensing agent (ICA) and another condensable fluid in the polymerization reactor using the gas chromatograph, calculate an equivalent partial pressure (($P_{ICA})_{equiv}$) of the ICA in the reactor from the concentration of the ICA and the other condensable fluid in the polymerization reactor, locating the reactor operation in a two dimension space defined by a reactor temperature dimension and a (($P_{ICA})_{equiv}$) dimension, and compare the location in the two dimensional space to an non-sticking regime defined as the space between an upper temperature limit (UTL) curve and a lower temperature limit (LTL) curve.

DETAILED DESCRIPTION

Figure 1A:
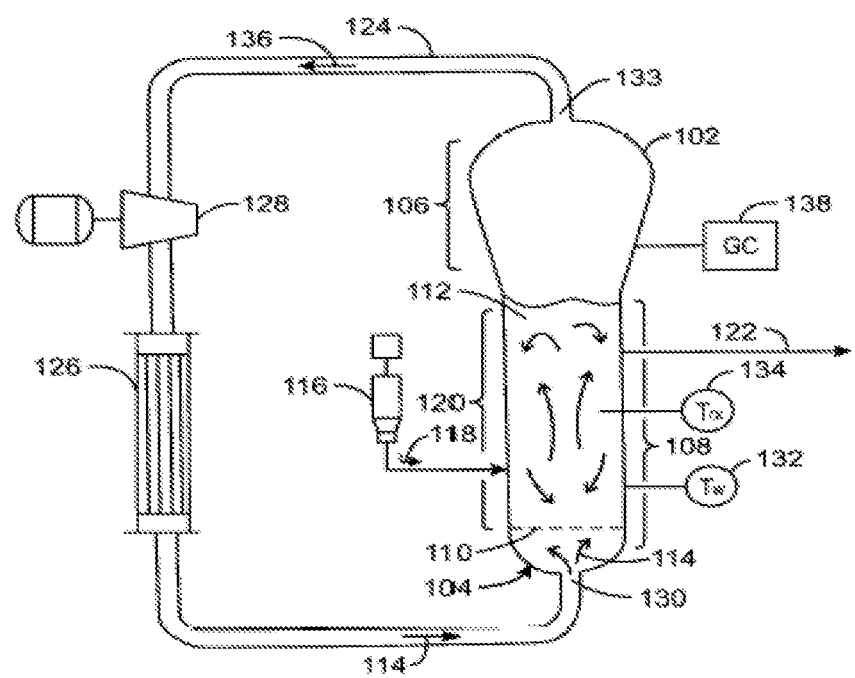
FIG. 1A is a simplified schematic of a reaction system that can be monitored and controlled in accordance with the methods described herein.

Described herein are systems and methods for determining a non-sticking operating regime (a "safe" regime) for a polymerization reactor, and operating the polymerization reactor within the non-sticking regime. As used herein, a non-sticking operating regime indicates a regime in which resin sticking is not problematic. The methods may include developing a model of the non-sticking operating regime which may be integrated into a control system or used on a separate system to recommend changes to control reaction parameters.

The parameters used in developing a model of the non-sticking operating regime may be based on values measured during experimental determinations of resin stickiness. For any single target resin, resin sticking can be measured as a function of temperature and the equivalent partial pressure of an induced condensing agent (ICA). For example, this may be performed by placing the resin in a stirred autoclave reactor with a measured amount of an ICA, such as isopentane ($iC_5$), and slowly increasing the temperature until the resin sticks, causing the stirrer to stall. A model can then be built that predicts sticking temperature as a function of the reactor temperature and an equivalent partial pressure of the ICA. The equivalent partial pressure is used to account for other condensable materials that may be present in the reactor, such as hexene and various isomers of hexene. The model is generally specific to the type of resin used.

The model and dew point of the ICA used in the polymerization reaction are used to determine a non-sticking operating regime. During the polymerization reaction, the reactor is controlled to hold the temperature and ICA concentration within the non-sticking operating regime. The non-sticking operating regime can provide guidance to help maximize production rates without agglomeration by controlling the reaction parameters to allow for increasing both temperature and ICA content, thus allowing the removal of more heat of reaction.

Throughout this disclosure, the expression "diluent" (or "condensable diluent" or "condensable diluent gas") denotes condensable gas (or a mixture of condensable gases) present in a polymerization reactor with polymer resin being produced. The diluent is condensable at the temperatures encountered in the process heat exchanger. Examples of diluents include induced condensing agents (ICAs), comonomers, isomers of comonomers, and combinations thereof. Such materials can include isobutane, isopentane, hexene, and other materials in the reactor.

With reference to a product being produced by a continuous reaction, the expression "instantaneous" value of a property of the product herein denotes the value of the property of the most recently produced quantity of the product. The most recently produced quantity typically undergoes mixing with previously produced quantities of the product before a mixture of the recently and previously produced product exits the reactor. In contrast, with reference to a product being produced by a continuous reaction, "average" (or "bed average") value (at a time "T") of a property herein denotes the value of the property of the product that exits the reactor at time T.

The expression "dry polymer resin" (or "dry version" of polymer resin) is used herein to denote polymer resin that does not contain substantial amounts of dissolved gas. An example of dry polymer resin is polymer that had been previously produced in a polymerization reactor and then purged to substantially all unreacted comonomers and ICAs that had been dissolved in the polymer at the time of production. As discussed herein, a dry version of polymer resin has significantly different melting behavior than would the same polymer resin if it were in the presence of a significant amount of condensable diluent gas and comonomer.

The expression polyethylene denotes a polymer of ethylene and optionally one or more $C_3$-$C_{10}$ alpha-olefins while the expression polyolefin denotes a polymer of one or more $C_2$-$C_{10}$ alpha-olefins.

FIG. 1A is a simplified cross-sectional view of a polymerization system 100 that can be monitored and controlled in accordance with embodiments. The polymerization system 100 includes a fluidized bed reactor 102. The fluidized bed reactor 102 has a bottom end 104, a top expanded section 106, a straight section 108, and a distributor plate 110 within the straight section 108. A fluidized bed 112 of granular polymer and catalyst particles is contained within the straight section 108. The bed is fluidized by the steady flow of recycle gas 114 through the distributor plate 110. The flow rate of the recycle gas 114 is regulated to circulate the fluidized bed 112, as illustrated in FIG. 1A.

The polymerization system 100 has a catalyst feeder 116 for controlling the addition of polymerization catalyst 118 to a reaction zone 120 within the fluidized bed 112. Within the reaction zone 120, the catalyst particles react with the ethylene and comonomer and optionally other reaction gases to produce the granular polymer particles. As new polymer particles are produced, other polymer particles are continually withdrawn from the fluidized bed through a product discharge system 122. After passing through the product discharge system 122, the polymer granules are degassed (or "purged") with a flow of inert nitrogen to remove substantially all of the dissolved hydrocarbon materials.

The polymerization system 100 also has a cooling loop which includes a recycle gas line 124, a circulating gas cooler 126, and a compressor 128, coupled with the fluidized bed reactor 102. During operation, the cooled circulating gas from the cooler 126 flows through inlet 130 into the fluidized bed reactor 102, then propagates upward through the fluidized bed 112 and out from the fluidized bed reactor 102 via outlet 132.

The expanded section 106 is also known as a "velocity reduction zone," and is designed to minimize the quantities of particle entrainment from the fluidized bed. The diameter of the expanded section 106 generally increases with the distance from straight section 108. The increased diameter causes a reduction in the speed of the recycle gas 114, which allows most of the entrained particles to settle back into the fluidized bed 112, thereby minimizing the quantities of solid particles that are "carried over" from the fluidized bed 112 through the recycle gas line 124.

One or more temperature sensors 134 may be located in the fluidized bed, and used with a control system and the cooling loop to control the temperature $T_{rx}$ of the fluidized bed 112 near the process set-point. Heated reactor gas 136, which carries heat energy from the fluidized bed reactor 102, is withdrawn from the outlet 132 and is pumped by the compressor 128 to the cooler 126 wherein the temperature of the heated reactor gases 136 is reduced, and any ICAs present are condensed to a liquid. The recycle gas 114 from the cooler 126, including any condensed liquids, flows to the reactor inlet 130 to cool the fluidized bed 112. Temperature sensors (not shown) near the inlet and outlet of the cooler 126 may provide feedback to a control system (FIG. 1B) to regulate the amount by which cooler 126 reduces the temperature of the recycle gas 114 entering the fluidized bed reactor 102.

The fluidized bed reactor 102 may also include skin temperature sensors 132, mounted in positions along a wall of the straight section 108 of the fluidized bed reactor 102 so as to protrude into the bed from the reactor wall by a small amount, e.g., about one eighth to one quarter of an inch. The skin temperature sensors 132 are configured and positioned to sense the temperature $T_w$ of the resin near the wall of the fluidized bed reactor 102 during operation.

The temperature sensors 134 in the fluidized bed 112 can include a resistance temperature sensor positioned and configured to sense bed temperature during reactor operation at a location within the fluidized bed reactor 102 away from the reactor wall. The resistance temperature sensor can be mounted so as to protrude into the bed more deeply than the skin temperature sensors 132, e.g., about 8 to 18 inches away from the reactor wall.

Other sensors and other apparatuses may be employed to measure other reaction parameters during a polymerization reaction. The reaction parameters may include instantaneous and bed-averaged resin product properties, e.g., melt index and density of the polymer resin product being produced by the polymerization system 100 during a polymerization reaction. Resin product properties are conventionally measured by periodically sampling the resin as it exits the reactor, e.g., about once per hour, and performing the appropriate tests in a quality control laboratory. The results of these tests may be used to adjust the model during operations.

Other measured reaction parameters may include reactor gas composition, e.g., concentrations and partial pressures of reactant gases, ICAs, inert gases, and isomers of other materials, such as nitrogen, inert hydrocarbon, and the like. The reactor gas composition may be measured with a gas chromatograph system 138.

The process control variables are controlled to obtain the desired productivity for the polymerization system 100 and properties for the resin. For example, the parameters used to control gas phase composition within the fluidized bed reactor 102 can include the concentration of ICAs and comonomer, the partial pressure of monomer, and the type and properties of catalysts, and the temperature of the reaction process. For example, it is known that a polymerization reaction during a transition may be controlled by controlling process control variables to ensure that the product, e.g., the granular resin, has properties compliant with an initial specification set at the start of the transition, the product produced during the transition ceases to comply with the initial specification set at a first time, and the product has properties compliant with a final specification set at the end of the transition. In the methods described herein, stickiness of the resin during the reaction is controlled by a control system adjusting (or regulating) the temperature and the equivalent partial pressure of the ICA used in the reaction.

Figure 1B:
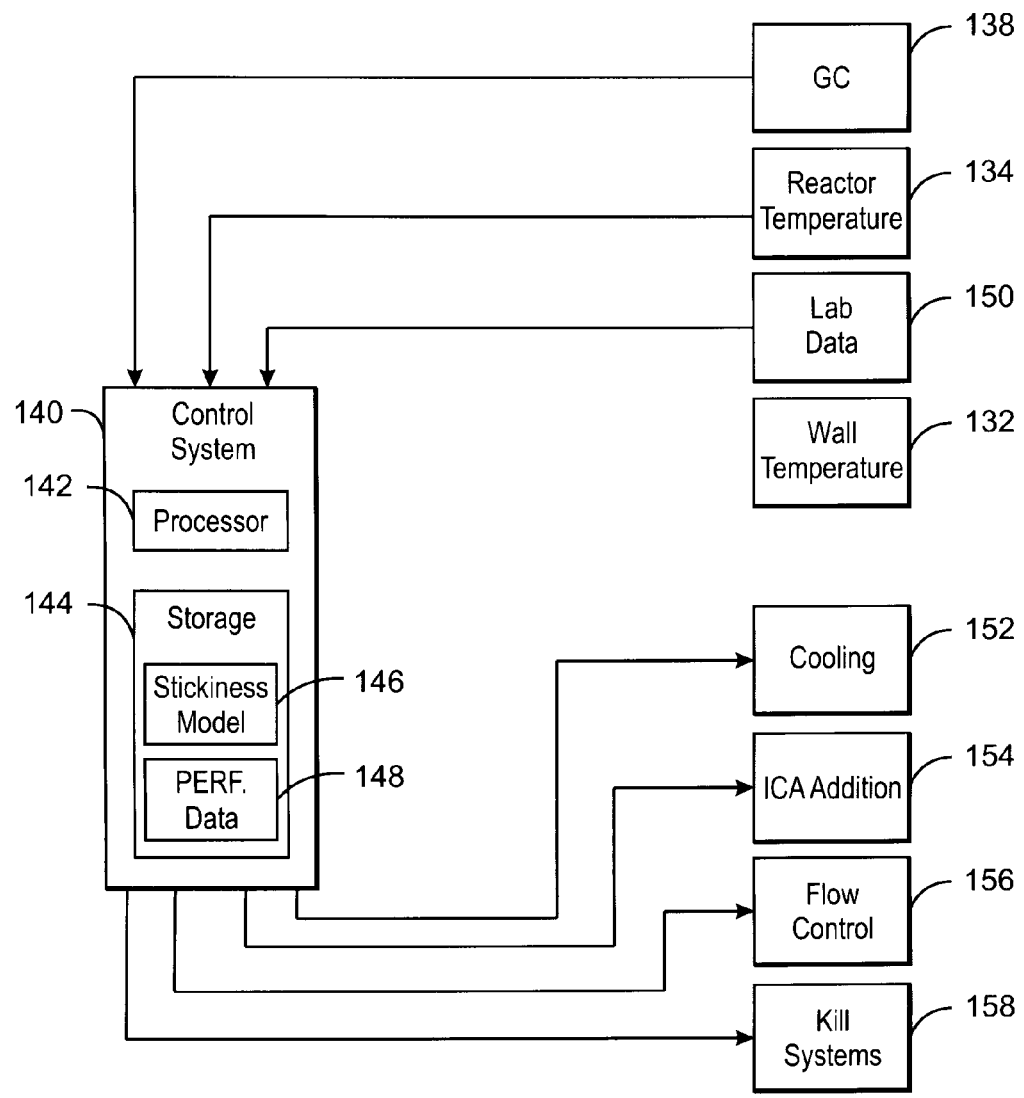
FIG. 1B is a simplified block diagram of a control system that can be used to control the reactor.

FIG. 1B is a simplified block diagram of a control system 140 that can be used to control the polymerization system 100. The control system 140 may be a distributed control system (DCS), a direct digital controller (DDC), a programmable logic controller (PLC), or any other suitable system or combination of systems capable of accepting data and proposing new control settings based on the model described herein. The control system 140 has a processor 142 that implements machine readable instructions from a storage system 144. Illustrative processors may include a single core processor, a multiple core processor, a virtual processor, a virtual processor in a cloud implementation, an application specific integrated circuit (ASIC), or any combinations of these systems. Illustrative storage devices 144 can include random access memory (RAM), read only memory (ROM), hard drives, virtual hard drives, RAM drives, cloud storage systems, optical storage systems, physically encoded instructions (for example, in an ASIC), or any combinations of these systems.

The storage system 144 may include a stickiness model 146 and a two dimensional representation, or map, of a non-sticking regime 148 that uses process and resin data to generate control settings for the polymerization system 100. Adjustments to control settings may be determined based on the output of temperature sensors 134 and 132, the GC 138, and lab data 150, among others. After determining new control settings, the control system 140 may make, or recommend, adjustments, for example, to the process cooling systems 152, the ICA addition and recycling systems 154, flow control systems 156, and kill systems 158, among others. Thus, the control variables can be used in concert with the model described herein to adjust reactor parameters to keep the reactor operations in a safe operating regime.

The methods described herein allow reactor production rates to be increased, e.g., by increasing reactor temperature and ICA, while avoiding the conditions in the reactor that may lead to excessive stickiness or the formation of liquids in the reactor. These methods use available process and resin property data, and can be implemented at plant sites either on-line, in process control systems, or off-line, e.g., using spreadsheets, data bases, or application specific programs.

As described herein, the model compensates for compounds that are present in the polymerization system 100 during polymerization reactions, such as polyethylene polymerization reactions using metallocene catalysts. For example, isomers of various co-monomers are relatively inert and may accumulate in reactors fitted with recovery systems. Because these isomers can be present in substantial amounts, they can have an impact on the stickiness. Accordingly, models that merely use the ICA concentration may not accurately predict the operating regimes that avoid sticking.

The gas chromatograph (GC) 138 can be used to provide composition data for isomers, in addition to the ICA. For example, the data from the GC may be analyzed to characterize separately the 1-hexene comonomer and the $C_6$ and $C_{6+}$ isomers of the comonomer in samples of cycle gas from the reactor. In some commercial polymerization reactions, isomer concentrations as high as 2.5 mole percent (of the total reactor gas) may be obtained in the reactor system, which can be substantially higher than the approximately 1 to 1.5 mole percent concentration of 1-hexene comonomer. At these levels, the isomers themselves (excluding the comonomer) can produce an increased tendency of the resin to stick and agglomerate. Such data can be incorporated into the model as a term called the "effective partial pressure" of the ICA. The effective partial pressure of the ICA adjusts the partial pressure of the ICA based on the amount of the ICA present.

Stickiness Testing to Develop Model Parameters

In U.S. Pat. No. 7,774,178 (the '178 patent), tests run in a pilot plant reactor, in the absence of polymerization, measured the resin stickiness temperature for a variety of Ziegler-Natta and metallocene catalyzed resins. The sticking temperature was measured for these resins with isopentane and without isopentane present in the cycle gas. The other process conditions held constant for each test included ethylene partial pressure, hydrogen concentration, and hexene concentration. Data from the bed sticking temperature experiments were compared to a melt initiation temperature (MIT) model which was used to specify a process temperature limit for polyethylene products based on resin properties and reaction conditions.

Figure 2A:
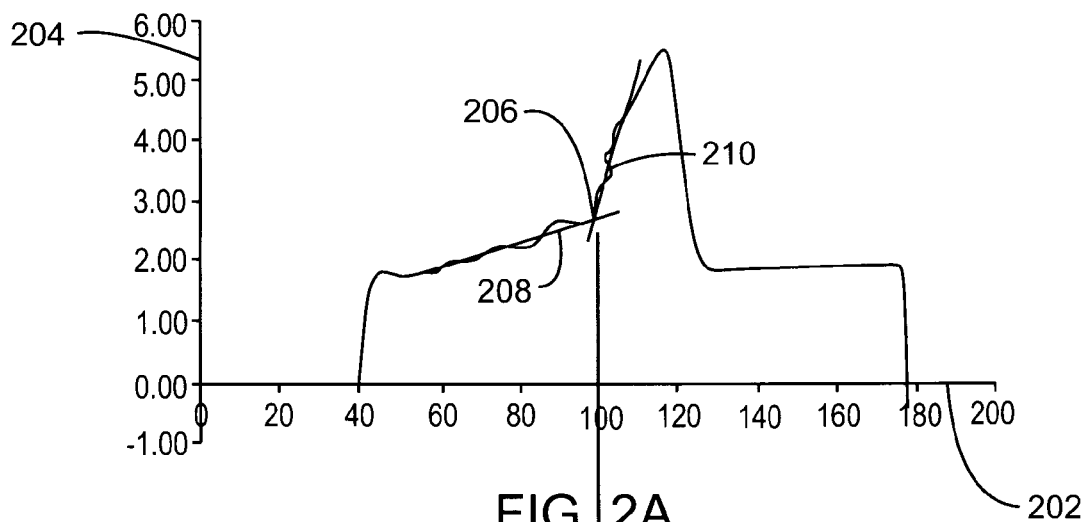
FIGS. 2A and 2B are plots showing a determination of melt initiation temperature (MIT) curve from a series of differential scanning calorimetry (DSC) curves.
Figure 2B:
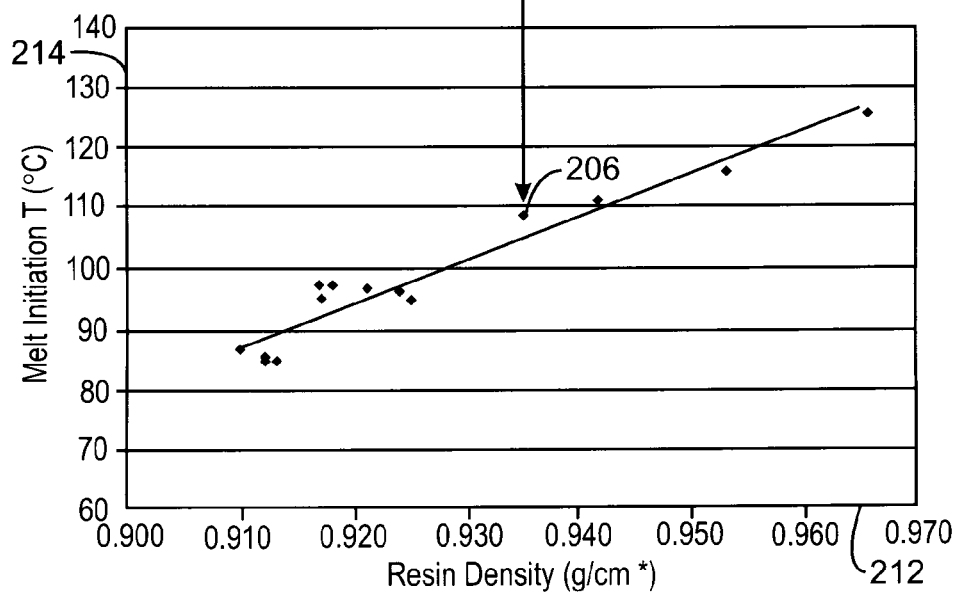

FIGS. 2A and 2B are plots showing a determination of melt initiation temperature (MIT) curve from a series of differential scanning calorimetry (DSC) curves. In FIG. 2A, the x-axis 202 represents the temperature in degrees Celsius, while the y-axis 204 represents the heat flow. An MIT 206 is identified as an interception point of the tangent lines 208 and 210 between two sections of the DSC curve. The steeper tangent line 210 represents a higher energy flow, which occurs as the resin changes phase. A sequence of MIT 206 values can be plotted against the density of the resin, as shown in FIG. 2B. In FIG. 2B, the x-axis 212 represents the density, while the y-axis 214 represents the values for the MIT of each of the individual resins, as determined by the DSC plots.

From the data, it was determined that an MIT model generally predicted a larger decrease in melt initiation temperature due to the presence of hydrocarbons compared to the change in sticking temperature seen experimentally, e.g., a displacement was seen between the MIT for the dry resin versus resin in the presence of hydrocarbons. A model was developed that correlated the sticking to theoretical properties of the resins involved. In several cases, the modeled change in MIT agreed with the observed change in sticking temperature.

In addition to the actual sticking temperatures, the '178 patent identified that isopentane depresses the sticking temperature of metallocene resins. At about 15 mol % isopentane in the cycle gas, the sticking temperature is depressed by 5-6° C. Further, the low concentrations of hexene co-monomer typically used with metallocene catalysts did not affect resin sticking temperature.

However, the '178 patent identified that high speed fluidized bulk density signal and skin thermocouple analysis did not provide any significant improvement in determining resin sticking temperature. Further, the melt-initiation temperature calculations did not accurately predict pilot plant determined sticking temperatures or the magnitude of the effect when isopentane was present in the reactor.

In another study conducted in the same pilot plant, resin stickiness temperature was measured using bed settling tests at different concentrations of condensing agents (isohexane and $iC_5$) for resins made with the various catalysts of the previous study to allow comparison with the previous results. It was determined that the equivalent concentration of the isohexane is approximately 2.5 times lower than that of isopentane ($iC_5$). These results can be used to validate the model created in this study to capture the operability window for metallocene catalysts.

Lab Experimental Setup and Sample Data

Stickiness tests were conducted in a testing device, as described herein, to gain a better understanding of the operability window in resin production with various metallocene catalysts. Through tests on a number of catalysts it was determined that unique parameters could be developed for each of a number of resins made using different catalysts. The stickiness risk associated with the resin made with these catalysts could be reduced by using a combination of temperature, MI/density/MFR targets, ethylene partial pressure, induced condensing agent ($iC_5$ or isohexane) concentration, and continuity additives.

Figure 3B:
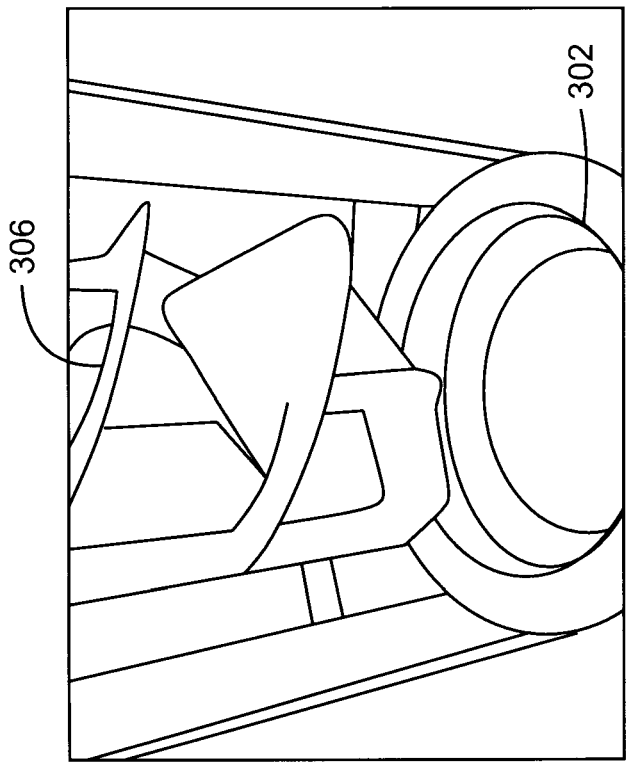
FIGS. 3A and 3B are drawings of a testing device used to measure stickiness temperature.
Figure 3A:
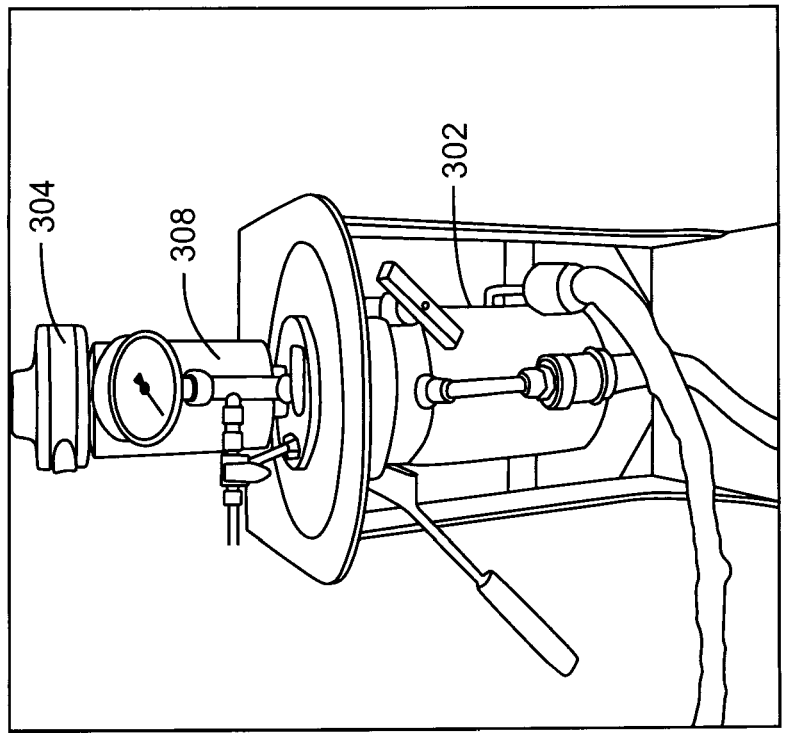

FIGS. 3A and 3B are drawings of a testing apparatus 300 that may be used to measure stickiness temperature. The apparatus 300 uses an autoclave reactor 302 that has a mixing motor 304. The mixing motor 304 rotates a mixer blade 306 that is inserted into a bed of resin in the autoclave 302. The temperature in the autoclave 302 is slowly raised until the torque required to turn the mixer blade 306 overcomes the torque available from the mixing motor 304, and the mixer blade 306 stops rotating, indicating the temperature at which the resin sticks or agglomerates. An illustrative mixing motor 304 that may be used is an air driven motor Model #2AM-NCC-16, manufactured by Gast Manufacturing, Inc. In FIG. 3A the mixing motor 304 turns a magnetic coupler 308, which in turn spins the mixer blade 306. An illustrative magnetic coupler 308 that may be used is a MagneDrive® 2, manufactured by Autoclave Engineers.

The testing device 300 can run the stickiness experiments at dry conditions, and also in the presence of induced condensing agents, such as isopentane ($iC_5$) and isohexane ($iC_6$). Although details are presented for a specific testing apparatus 300, it will be understood that any device capable of consistently measuring the torque of a rotating mixer blade can be used to develop the model for a particular resin.

Figure 4:
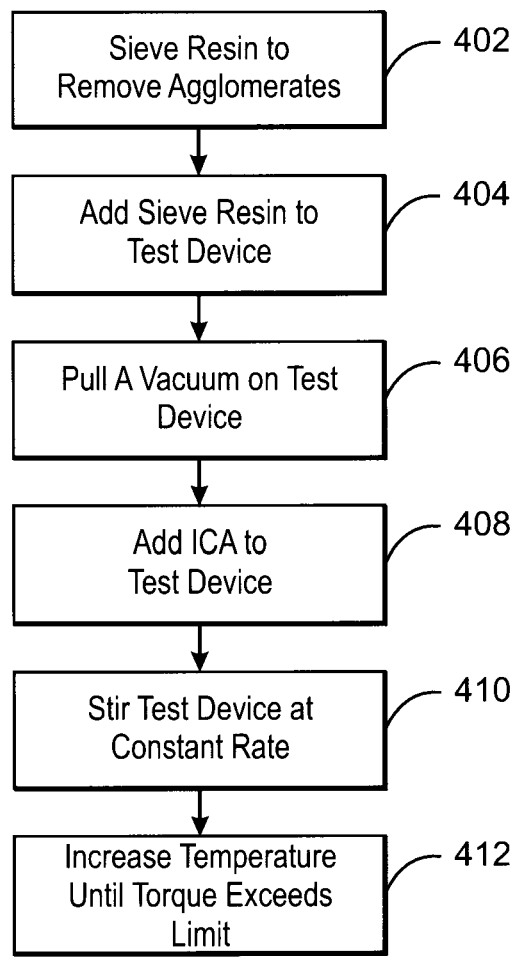
FIG. 4 is a process flow diagram showing a method for measuring stickiness temperature.

FIG. 4 is a process flow diagram showing a method 400 for measuring stickiness temperature. The method 400 may be used, for example, with the testing device 300 of FIGS. 3A and 3B. The method 400 begins at block 402 with the sieving of a resin sample. The sieving removes agglomerates that can interfere with the stickiness measurements. For example, the resin sample can be sieved through a number 12 mesh (having about 1.68 mm openings). At block 404, a measured amount of the resin is added to the testing device. For example, about 300 g of sieved polymer resin can be added to the testing device 300 of FIGS. 3A and 3B. At block 406, the testing device is placed under a vacuum prior to adding an ICA, such as $iC_5$, to ensure proper measurement of the partial pressure of the ICA. At block 408 an amount of ICA is added to the testing device to reach a predicted partial pressure. For example, using the testing device 300 of FIGS. 3A and 3B, five levels are tested for each resin tested, corresponding to 0, about 25 cc, about 50 cc, about 100 cc, or about 200 cc of added $iC_5$. At block 410, the testing device is then stirred at a constant rate. For example, using the air-operated stirring motor 304 of the testing device 300 of FIGS. 3A and 3B, a constant nitrogen pressure of about 30 psi (about 207 kPa) is applied to hold a constant torque.

At block 412, the reactor temperature is increased slowly until a torque limit is exceeded. For example, using the testing device 300 of FIGS. 3A and 3B, when the torque limit is exceeded the mixing motor stops, indicating the stickiness temperature. The testing is not limited to the stopping of an air-operated mixing motor. For example, a torque measurement device may be used to measure the torque applied to the testing device to determine when the torque exceeds a preset target.

Figure 5:
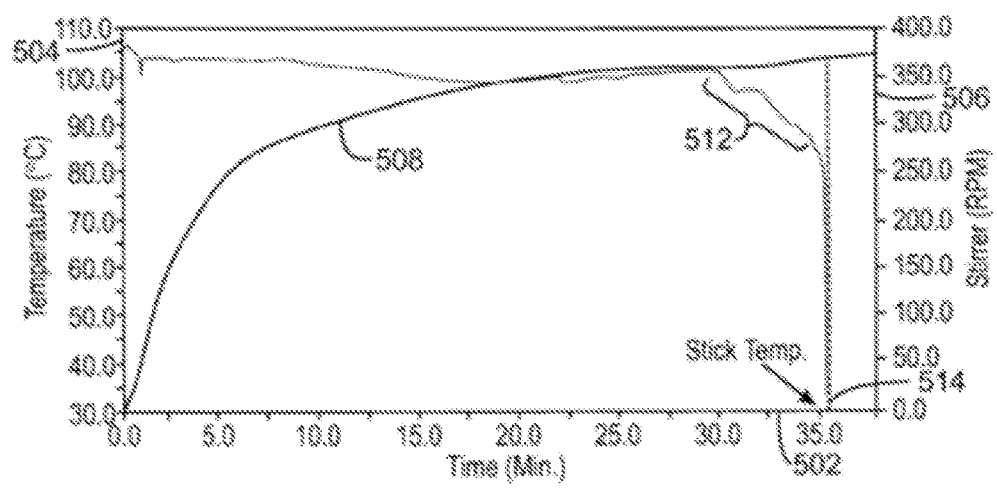
FIG. 5 is a plot of temperature and stirrer speed during a stickiness temperature test in the testing device of FIG. 3.

FIG. 5 is a plot 500 of temperature and stirrer speed during a stickiness temperature test in the testing device 300 of FIGS. 3A and 3B. The x-axis 502 represents the test duration in minutes, while the left y-axis 504 represents the temperature of the testing device in degrees Celsius. The right y-axis 506 represents the mixer speed in RPM. During the test, the temperature 508 in the reactor is slowly increased. For most of the test, the mixer speed is relatively constant. However, as the resin starts to agglomerate, the mixer speed starts to slow, as indicated by reference number 512, before stopping. The point at which the mixer speed drops to zero is the stickiness temperature 514. As noted, the test is repeated at a number of different addition levels of the ICA (e.g., $iC_5$), providing data that can be used to characterize the sticking temperature.

Figure 6:
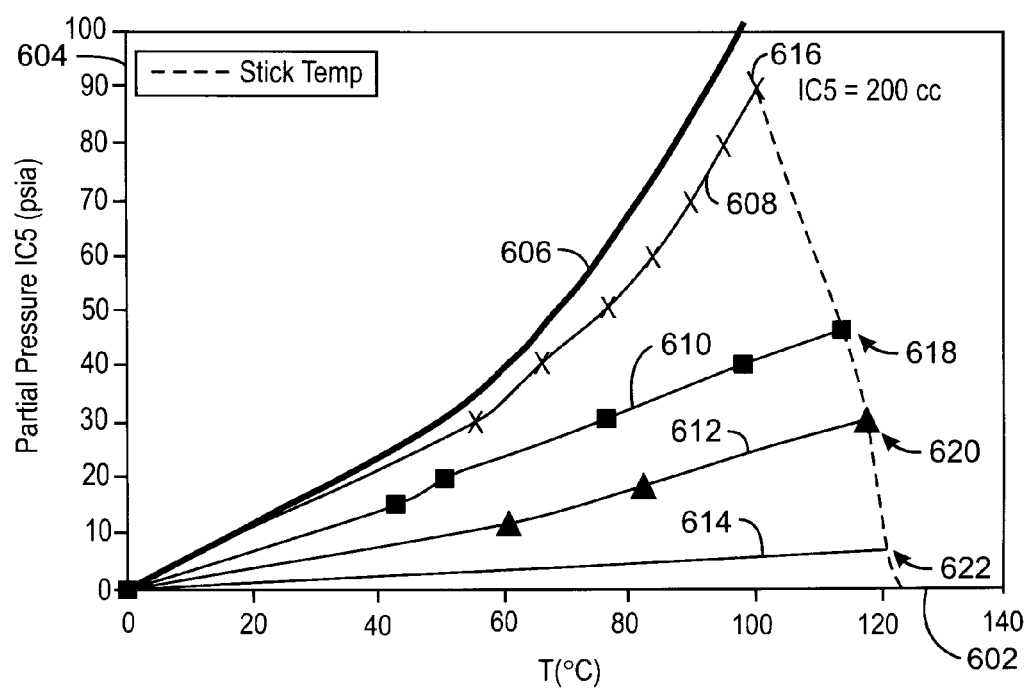
FIG. 6 is plot of partial pressure of isopentane ($iC_5$) versus testing device temperature, showing sticking for a resin made using a metallocene catalyst.

FIG. 6 is plot 600 of partial pressure of isopentane ($iC_5$) versus testing device temperature, showing sticking for a resin made using a metallocene catalyst. In this example, the resin has a melt index (MI) of 41.72, a density of 0.954 g/cc, and a melt flow ratio (MFR) of 18.5. In the plot 600, the x-axis 602 represents the temperature in degrees Celsius, while the y-axis 604 represents the partial pressure of $iC_5$.

A reference curve 606 indicates the partial pressure of the $iC_5$ at the testing device temperature. Subsequent curves 608, 610, 612, and 614 indicate the partial pressure of the resin after the addition of about 200 cc of $iC_5$ 608, about 100 cc of $iC_5$ 610, about 50 cc of $iC_5$ 612, and about 25 cc of $iC_5$ 614. The points 616, 618, 620, and 622 at which each curve ends indicates the stickiness temperature at the respective partial pressure.

Figure 7:
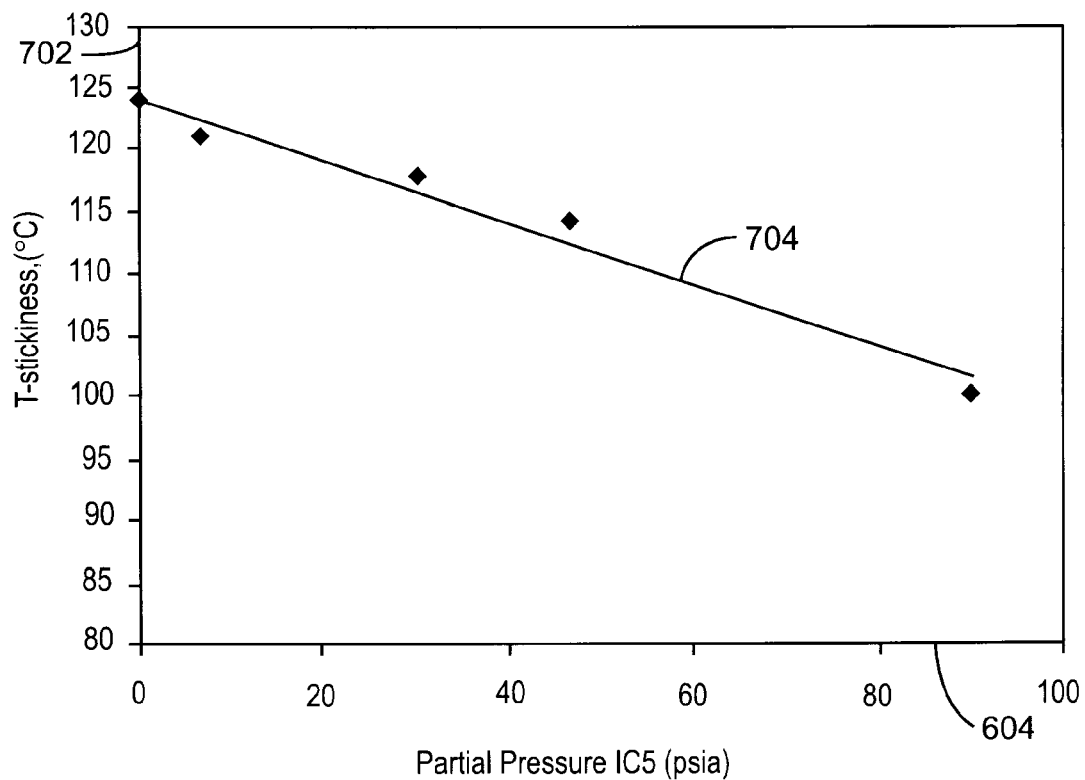
FIG. 7 is a plot of stickiness temperature of the resin versus the partial pressure of $iC_5$ for the resin described with respect to FIG. 6.

FIG. 7 is a plot 700 of stickiness temperature of the resin versus the partial pressure of $iC_5$ for the resin described with respect to FIG. 6. Like numbered items are as discussed with respect to FIG. 6. The y-axis 702 represents the stickiness temperature in degrees Celsius. The resin stickiness temperature 704 provides a substantially linear correlation with the $iC_5$ concentration in the reactor.

Model Development

The stickiness tests described with respect to FIGS. 1-7 were performed on 12 different resins generated by a three metallocene catalysts, herein termed Catalyst 1, Catalyst 2, and Catalyst 3. For each resin, five different $iC_5$ levels were run to get a reliable correlation, as described with respect to FIG. 7. Resin density varied from 0.912 g/cc to 0.954 g/cc, MI varied from 0.5 to 42 g/10 min, and MFR varied from 16 to 36. The stickiness temperature was correlated as a linear function of $iC_5$ concentration. The results from the testing allowed the development of a model to predict the resin sticking temperature $T_{stick}$ that encompassed the metallocene catalyst systems tested. The coefficients of the linear functions were generated as a function of resin density, MI and MFR. Although the test resins were made using metallocene catalysts, as the model is empirically generated, the parameters may be adjusted for other catalyst systems, for example, by repeating the model development runs for those resins.

The basic model equation used to predict the resin sticking temperature for resins generated by these three catalysts is shown in Eqn. 1.

$$T_{stick} = -C_1 * (P_{iC5})_{equiv} + C_2 \qquad \text{Eqn. 1}$$

In Eqn. 1, the parameters identified as $C_1$ and $C_2$ are determined as shown in Eqns. 2 and 3, respectively. The data collected from the stickiness temperature measurements described above can be combined with laboratory data and used in a multivariable least squares analysis to generate the coefficients for the equations.

$$C_1 = 1.175 \times 10^{-3} * D^{-59.736} * MI^{0.641} \qquad \text{Eqn. 2}$$

$$C_2 = 180.6 * D^{3.07} * MFR^{-0.077} \qquad \text{Eqn. 3}$$

In Eqns. 2 and 3, D represents the density of the resin in g/cc, MI represents the melt index of the resin (as measured by ASTM D 1238 190° C. with 2.16 kg weight), and MFR represents the ratio of the HLMI (as measured by ASTM D 1238 at 190° C. with 21.6 kg weight) to the MI. The excess isomers of the hexane, e.g., the hexanes, are accounted for by adjusting the partial pressure of the ICA ($iC_5$) to form an effective partial pressure, as shown in Eqn. 4.

$$(P_{iC5})_{equiv} = P_{iC5} + 2.7 * P_6 \qquad \text{Eqn. 4}$$

In Eqn. 4, $P_6$ represents the partial pressure of the hexanes in the reactor at the operating temperature. The coefficient, 2.7, can be changed to reflect the ratio of the partial pressure of the hexanes to the partial pressure of the $iC_5$, or other ICA used.

Figure 8A:
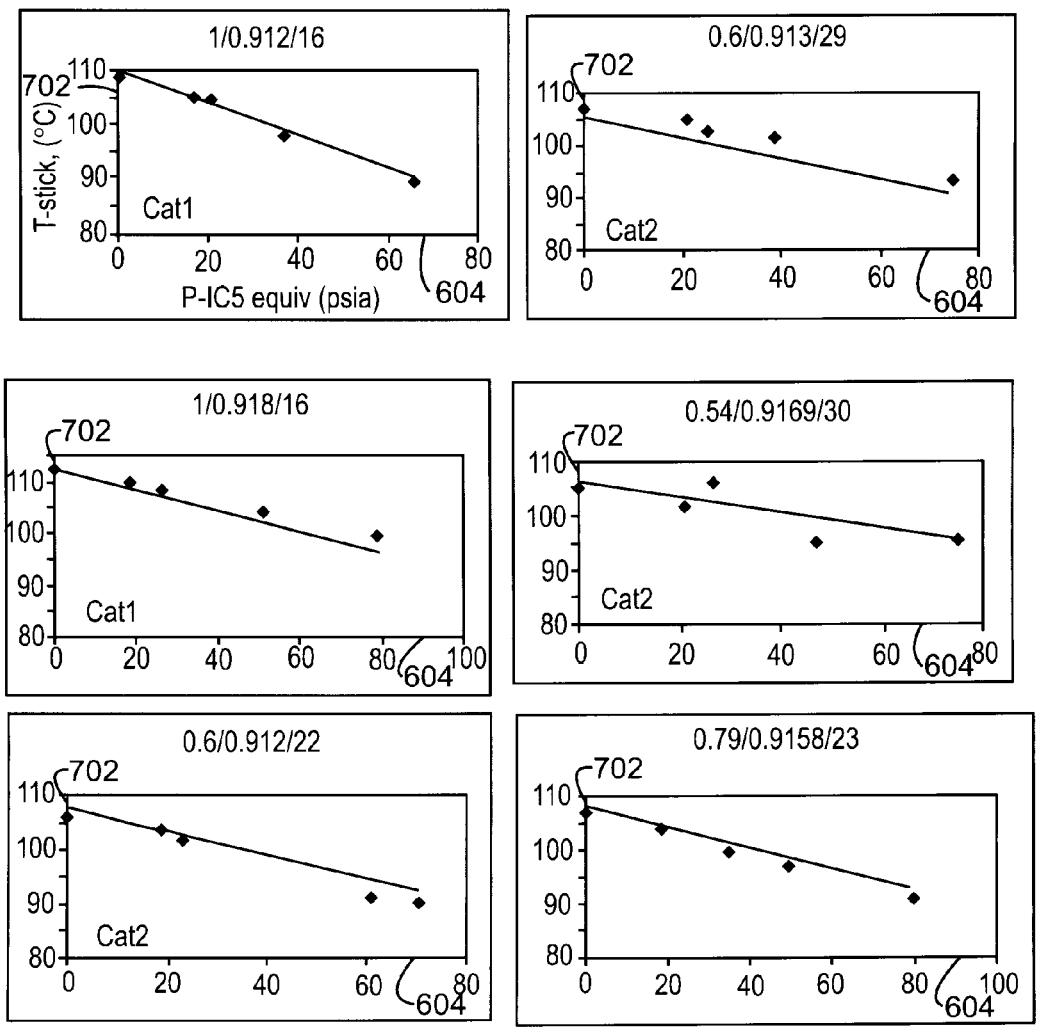
FIGS. 8A and 8B show plots of the model predictions versus experimental data for various resins.
Figure 8B:
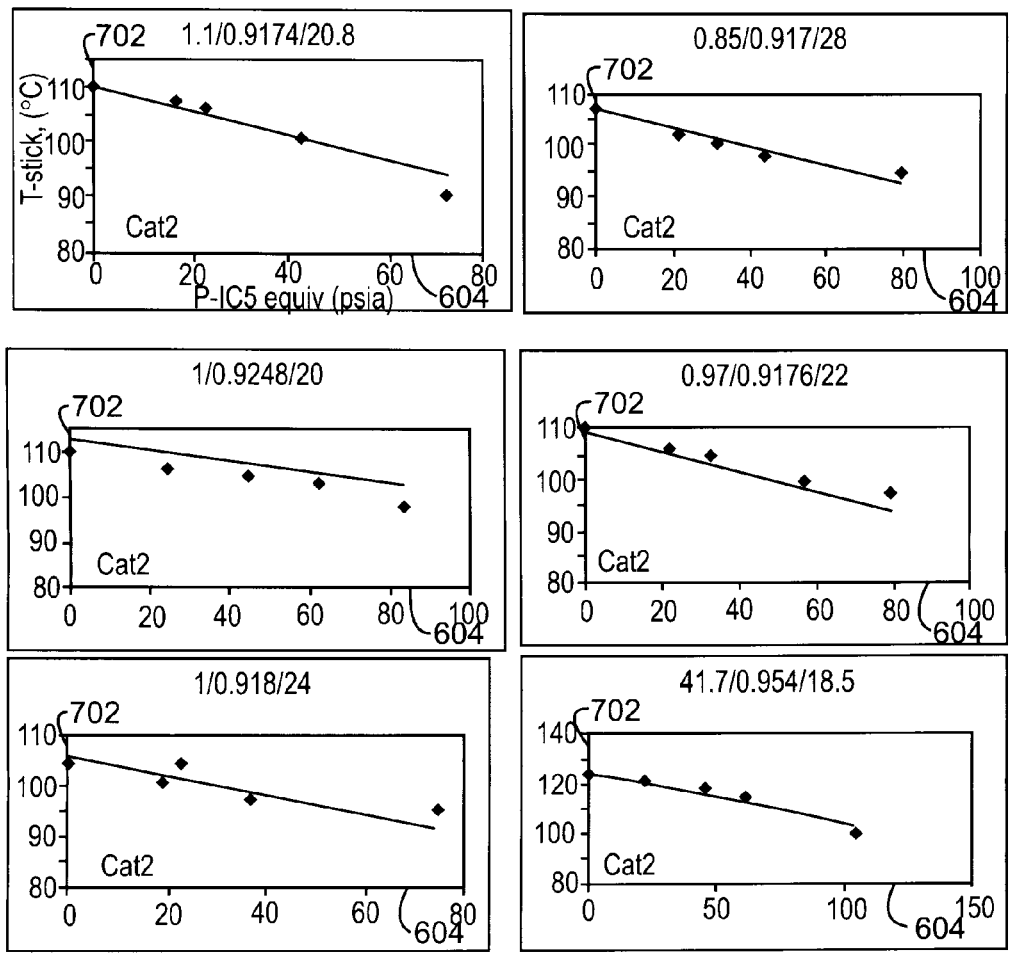

FIGS. 8A and 8B show plots of model versus experimental data for the various resins. Like numbered items are as defined with respect to FIGS. 6 and 7. For each plot, the individual resin parameters are shown above the plot as MI/Density/MFR. In each plot, the individual measurements are shown as the data points, while the output from the model is shown as a line. As seen in FIGS. 8A and 8B, the model substantially predicts the experimental data from lab experiments for resins formed by the different metallocene catalysts.

Figure 9:
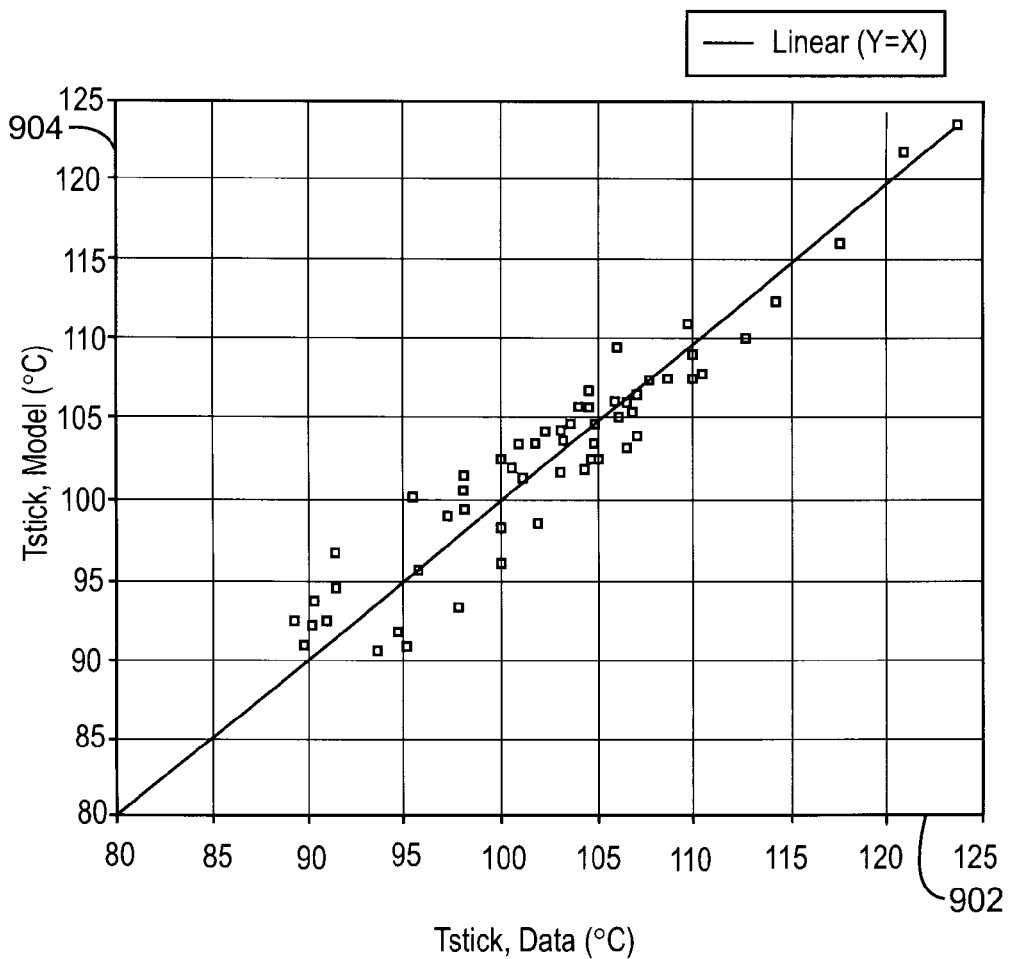
FIG. 9 is a plot of experimental stickiness temperature versus predicted stickiness temperature for a variety of resins.
Figure 10:
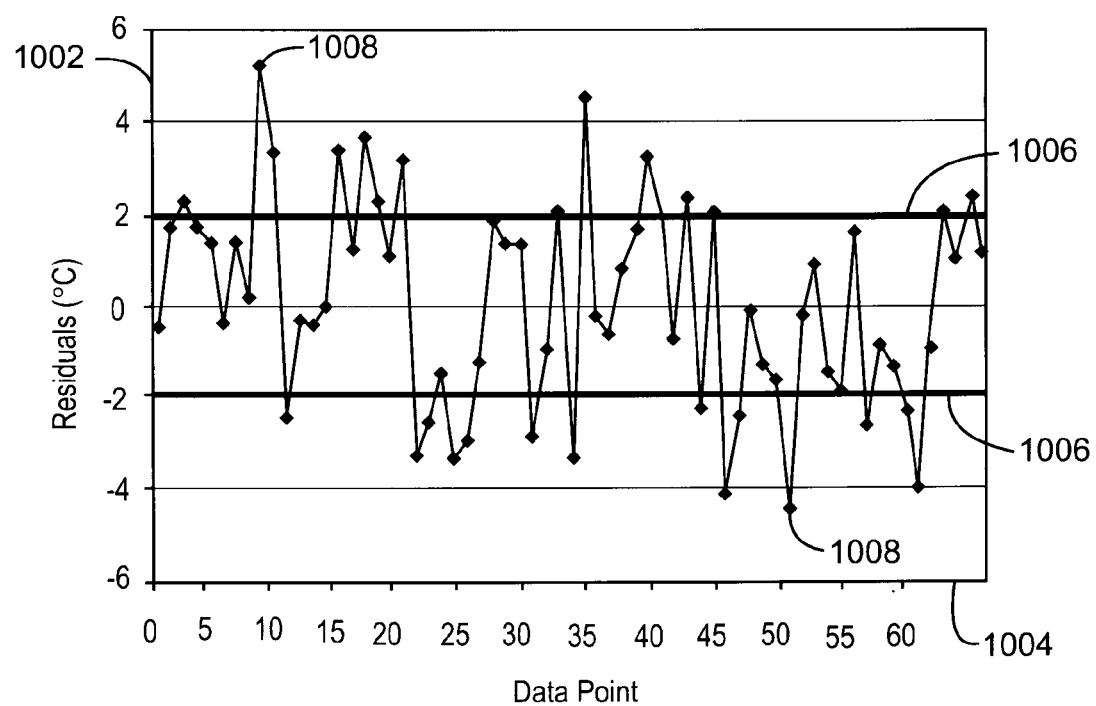
FIG. 10 is a plot of residuals for each of the data points of FIG. 9 showing average errors and maximum errors.

FIGS. 9 and 10 illustrate the accuracy of the model. FIG. 9 is a plot 900 of experimental stickiness temperature 902 versus predicted stickiness temperature 904 for a variety of resins. FIG. 10 is a plot 1000 of residuals 1002 for each of the data points 1004 of FIG. 9 showing average errors 1006 and maximum errors 1008. The model has an average error of 2° C. and the maximum error is about 5° C.

Stickiness Temperature Model Validation

The properties of the resins used in the experiments, reactor conditions, experimental stickiness temperatures, and model predictions are tabulated in Table 1, below. The temperature at which fluidization was lost is shown in the column labeled "T-s, exp, ° C." The comparative value predicted by the model described herein is shown in the column labeled "T-s, model, ° C."

Figure 11:
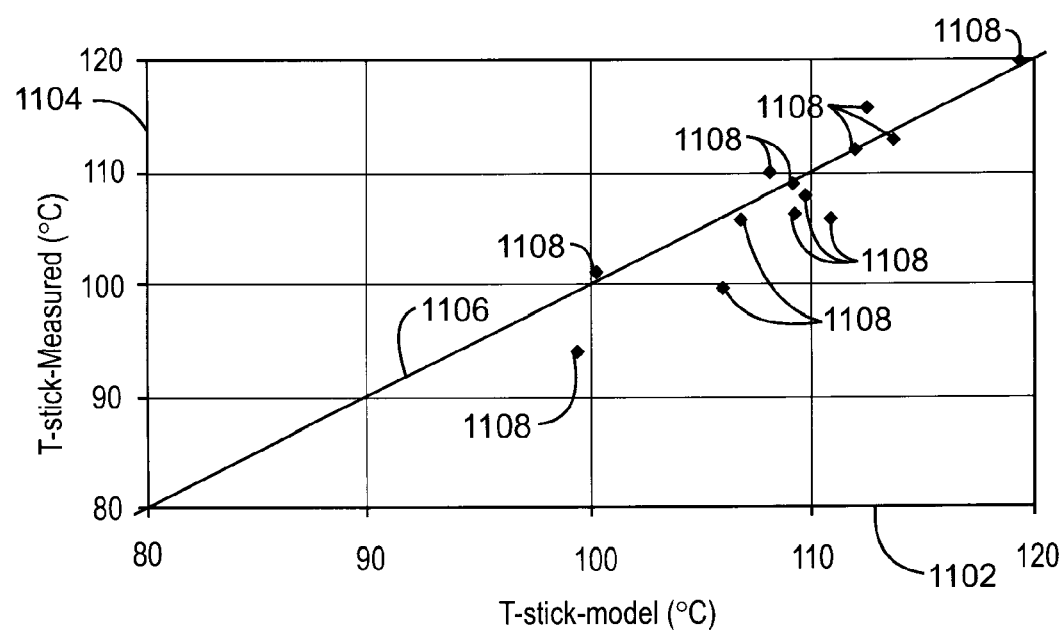
FIG. 11 is a plot of experimental data versus model predictions.

FIG. 11 is a plot 1100 of experimental data versus model predictions. In FIG. 11, the x-axis 1102 represents the predicted value of the stickiness temperature, while the y-axis 1104 represents the measured stickiness temperature. The experimental stickiness temperatures from the pilot plant runs, shown as points 1108, and the model predictions, line 1106, show substantial agreement.

Generally, the model predictions had an average error of 3° C. from the bed settling experiments. Considering the size difference with in the experimental setup and variations within the reactor conditions, the model effectively predicts the measured data.

TABLE 1

Polyethylene Resin Sticking Temperature Tests

| Resin | Density | MI | MFR | $iC_5$ mol % | C6 mol % | P-$iC_5$ | T-s, exp, ° C. | T-s, model, ° C. |
|---|---|---|---|---|---|---|---|---|
| Catalyst 3 | 0.9194 | 0.96 | 38.5 | 0.036 | 0.000 | 0.112 | 110 | 108 |
| Catalyst 1 | 0.9117 | 1.05 | 15.6 | 0.032 | 1.185 | 10.052 | 106.5 | 109 |
| Catalyst 2 | 0.9189 | 1 | 26.4 | 0.015 | 0.000 | 0.047 | 106 | 111 |
| Catalyst 2 | 0.9164 | 0.84 | 23.2 | 14.1 | 1.333 | 55.047 | 101 | 100 |
| Catalyst 1 | 0.916 | 0.98 | 15.9 | 0.023 | 0.000 | 0.072 | 113 | 114 |
| Catalyst 1 | 0.9171 | 0.99 | 15.9 | 0.027 | 1.259 | 10.658 | 112 | 112 |
| Catalyst 1 | 0.9162 | 1 | 20 | 0.027 | 1.259 | 10.658 | 108 | 110 |
| Catalyst 2 | 0.9354 | 6.6 | 20 | 0.032 | 0.000 | 0.100 | 120 | 119 |
| Catalyst 2 | 0.9353 | 6.43 | 20.1 | 8.7 | 0.667 | 32.655 | 116 | 112 |
| Catalyst 2 | 0.9187 | 1.09 | 32.8 | 0.031 | 0.000 | 0.096 | 109 | 109 |
| Catalyst 2 | 0.9187 | 1.12 | 32.8 | 0.031 | 1.333 | 11.292 | 106 | 107 |
| Catalyst 2 | 0.9169 | 0.66 | 33.6 | 0.032 | 1.778 | 15.028 | 100 | 106 |
| Catalyst 2 | 0.9168 | 0.67 | 33.5 | 14.4 | 1.148 | 54.425 | 93.95 | 99.35 |

The model predictions were validated against bed settling experiments done in a pilot plant scale, gas-phase fluidized bed reactor. In these experiments, a non-reacting run was performed to determine the temperatures at which the resin agglomerated. The test was started by drying the reactor with a high purity nitrogen purge at elevated temperatures, e.g., greater than about 75° C. The test resin sample was passed through a 10-mesh screen (having about 0.25 mm openings) to remove agglomerates, and then charged to the reactor. Using the nitrogen flow, the resin was dried to about 10 parts-per-million by volume (ppmv) of water. The test resin was heated to at least 85° C. and the reactor conditions were adjusted to the desired ethylene partial pressure, comonomer concentration, and ICA ($iC_5$) concentration. A sample was then collected for measurement of melt flow and particle size.

The resin temperature was then increased by about 2° C. or 3° C. at a rate of about 1° C. every 30 minutes. Once the target temperature was reached, the temperature was allowed to stabilize for 30 minutes. The fluidized bulk density, bed weight, and skin temperature were noted. The circulation compressor was then turned off, and the bed was allowed to settle on the distributor plate. After about 15 minutes, the circulation compressor was turned back on to fluidize the resin. If the bed did not fluidize, the test was ended. If the bed did fluidize, the reactor was given about five minutes to stabilize before initiating the next increase in temperature. The procedure was repeated until the bed agglomerated to the point that fluidization was lost.

Using the Stickiness Temperature Model to Generate a Non-Sticking Operating Regime The stickiness temperature model can be combined with dew point calculations to define an operability window, e.g., a non-sticking operating regime in a map of reactor operations, for the manufacturing of resins made with the currently tested metallocene catalysts. Other models may be created that are specific to resins made by other metallocene catalysts, Ziegler catalysts, or chromium catalysts, among others. As the model is based on the empirical measurements of resin properties and reactor conditions, resins generated from mixtures and combinations of catalysts may also be made.

Figure 12:
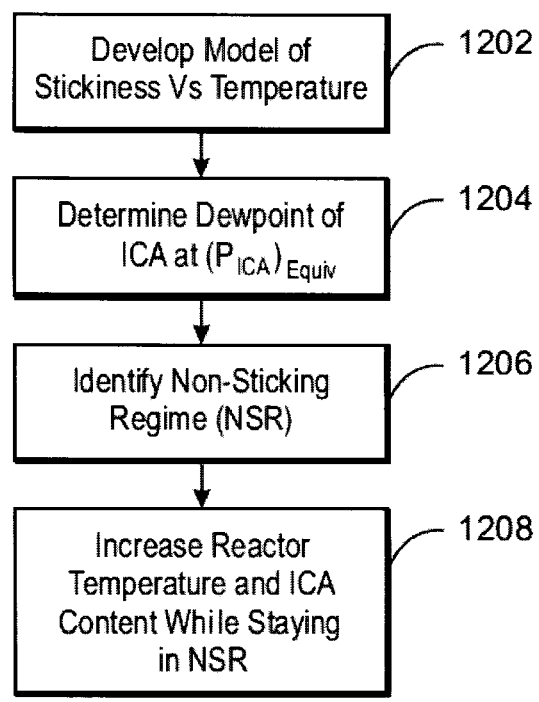
FIG. 12 is a process flow diagram of a method for operating a reactor in a non-sticking regime.

FIG. 12 is a process flow diagram of a method 1200 for operating a reactor in a non-sticking regime. The method 1200 starts at block 1202 with the development of a model for the stickiness temperature. The model may be developed, for example, using measurements made with the method 400 discussed with respect to FIG. 4, and fitting the measured data to develop parameters for Eqns. 1-4 discussed with respect to FIG. 7. At block 1204, a dew point for the ICA (e.g., $iC_5$) can be determined at each of the equivalent partial pressures for the ICA. The dew point indicates the conditions of temperature and equivalent partial pressures of ICA below which liquid ICA starts to condense in the reactor. The formation of liquid ICA can increase the likelihood of agglomeration and case operational issues by condensing in instrumentation taps.

Figure 13:
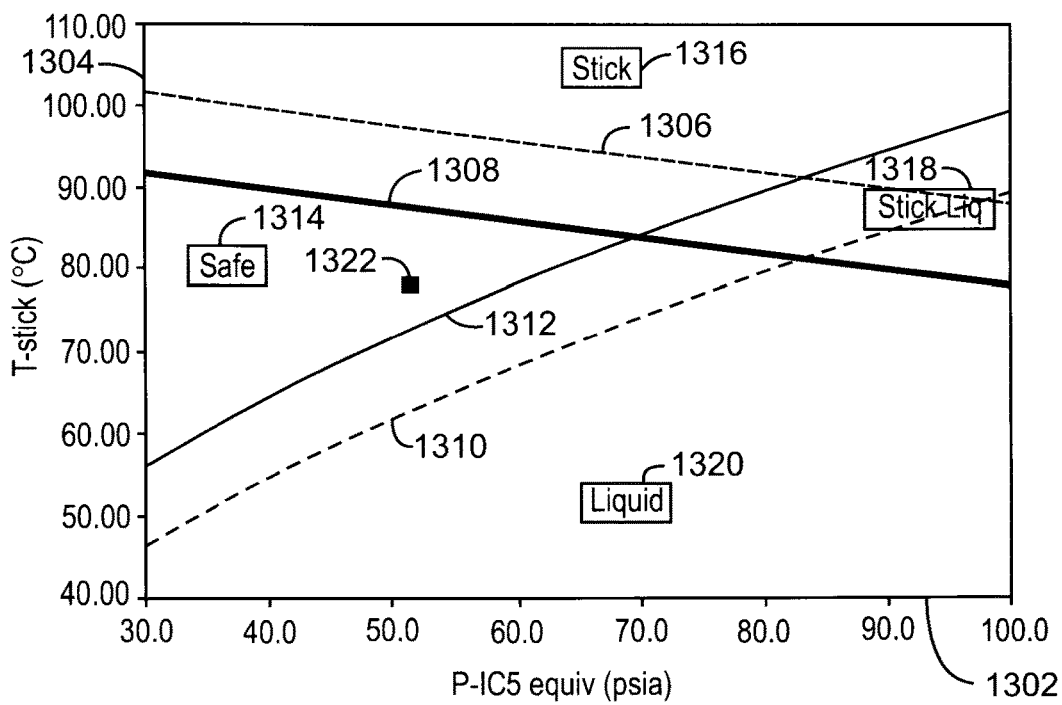
FIG. 13 is a plot of an operability window for avoiding agglomeration of resins.

At block 1206, the stickiness temperature and the dew point can be used to identify a non-sticking regime, as discussed with respect to FIG. 13. Once a non-sticking regime is established, at block 1208 the ICA concentration and temperature can be adjusted to remain in the safe operating regime. For example, a startup of a new resin production run may be conducted at a slow initial production rate. The ICA concentration, temperature, or both may then be slowly increased to increase the production rate, while keeping the reactor within the safe operating regime. If a reactor upset causes operations to leave the non-sticking regime, or indicates that sticking may be imminent, the control system can recommend changes to force the operations back into the non-sticking regime, for example, by lowering or raising the temperature, by decreasing the amount of ICA returned from the recycle system, or by injecting a kill solution to slow or stop the reaction, among others. The control system may identify problematic operations before the reactor is shut down by agglomeration. The method 1200 is discussed further with respect to FIGS. 13-19.

FIG. 13 is a plot 1300 of an operability window for avoiding agglomeration of resins. As shown in the plot 1300, the temperature of the reactor and the equivalent partial pressure of the ICA define a two dimensional space, or map, for reactor operations. In the plot 1300, the x-axis 1302 represents the equivalent partial pressure of the ICA, i.e., $iC_5$ in this example. The equivalent partial pressure of the $iC_5$ can be calculated using the formula in Eqn. 4. The y-axis 1304 represents the sticking temperature in degrees Celsius. The predicted stickiness temperature ($T_{stick}$) 1306 from the model is plotted as the upper dashed line. To provide a limit, the $T_{stick}$ 1306 is adjusted to a lower value to provide a safety margin, using Eqn 5.

$$T_{reactor,max} = T_{stick} - UTD_{max} \quad \text{Eqn. 5}$$

In Eqn. 5, $T_{reactor,max}$ represents the maximum operating temperature that can be used without a substantial risk of agglomeration. $UTD_{max}$ represents an upper temperature delta that provides a buffer between the stickiness temperature measured in the experiments and the temperature at which the stickiness may actually begin. Typically, a 10° C. margin is allowed below the stickiness temperature for the reactor to operate safely. Thus, the value of the $T_{reactor,max}$ provides the upper temperature limit 1308 for the reactor.

In FIG. 13, the dew point ($T_{dew}$) 1310 is plotted as the lower dashed line. Similar to the maximum operating temperature, the dew point 1310 can be adjusted to provide a wider margin of safety using Eqn. 6.

$$T_{reactor,min} = T_{dew} + LTD_{max} \quad \text{Eqn. 6}$$

In Eqn. 6, $LTD_{max}$ is a lower temperature delta that accounts for capillary condensation, which occurs about 10° C. above the actual dew point of the ICA in the reactor. The value of the $T_{reactor,min}$ provides the lower temperature limit 1312 of the reactor.

The upper temperature limit 1308 and the lower temperature limit 1312 define a non-sticking regime 1314 for the reactor within the two dimensional space. Another area defined by these limits 1308 and 1312 is a sticking regime 1316 in which the resin begins to melt and therefore becomes sticky. Other areas include a stick+liquid regime 1318, in which both resin melting and $iC_5$ (or other ICA) condensation make the resin sticking more likely. Below the upper temperature limit 1308 and the lower temperature limit 1312 is a liquid regime 1320, in which the $iC_5$ (or other ICA) starts to condense and make the resin sticky.

The square 1322 represents a current reactor condition, mapped by the temperature and equivalent partial pressure of the $iC_5$. To operate the reactor without agglomeration, an operator maintains the square 1322 representing the current reactor conditions within the non-sticking regime 1314. The operator can change reactor parameters to move the square 1322 towards the neck, at which the limits 1308 and 1312 meet, to increase productivity, while still staying within the non-sticking regime 1314. It can be noted that as the square 1322 is pushed closer to the neck, operations becomes less flexible and the room for error dwindles, making process upsets, such as temperature and concentration excursions, more problematic.

Non-Sticking Operating Regime Model Validation

A series of polymerization experiments were conducted in a pilot plant reactor to determine the stickiness temperature as a function of $iC_5$ concentration of the low density (0.918 g/cc) and VLDPE (0.912 g/cc) resins made with both Catalyst 1 and Catalyst 2. The data from the run are shown in Table 2, and the results may be used to validate the operability window predicted by the model. Also included are the data from two commercial runs with Catalyst 1 in a commercial size production facility. Each of the cases is illustrated with respect to one of the following figures, as indicated in Table 2.

TABLE 2

Experimental Data from Pilot Plant and Commercial Plant Runs

Figure 14:
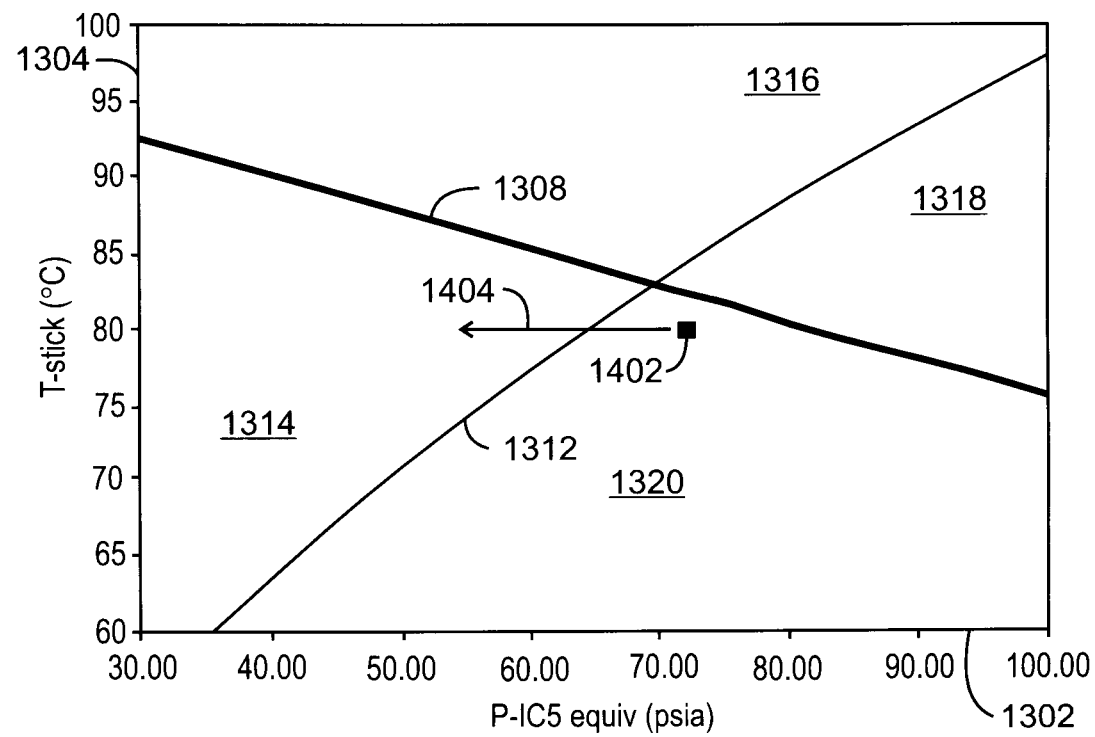
FIG. 14 is a plot of a pilot plant run showing operation in a liquid regime in a first case study.
Figure 15:
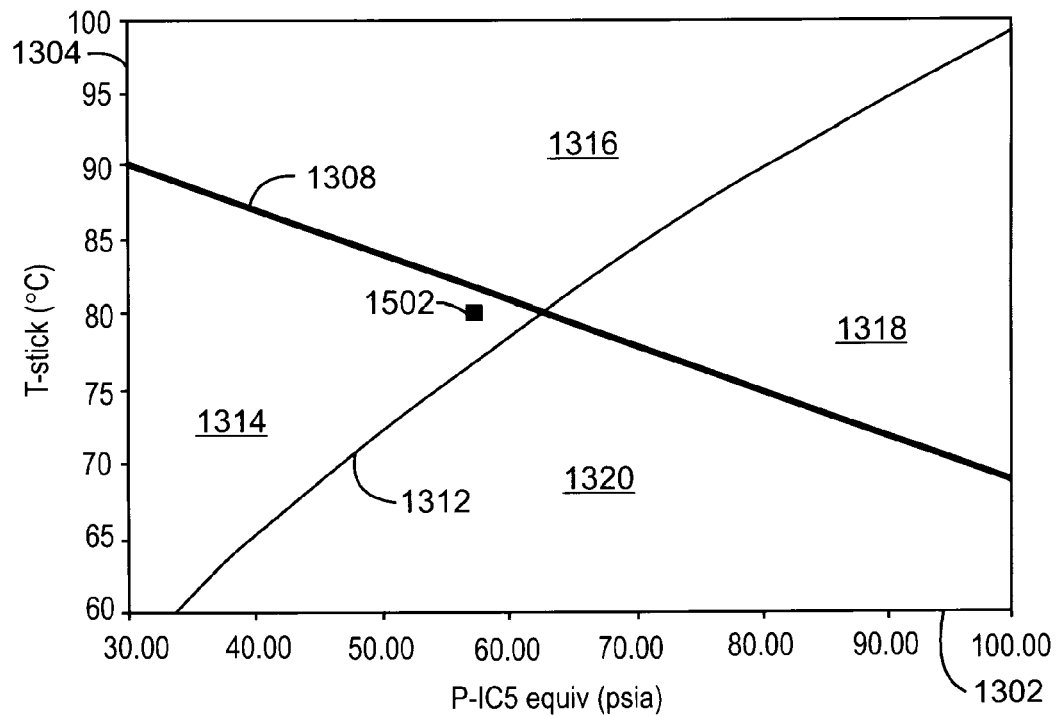
FIG. 15 is a plot of operations within a non-sticking regime during a commercial plant run.
Figure 16:
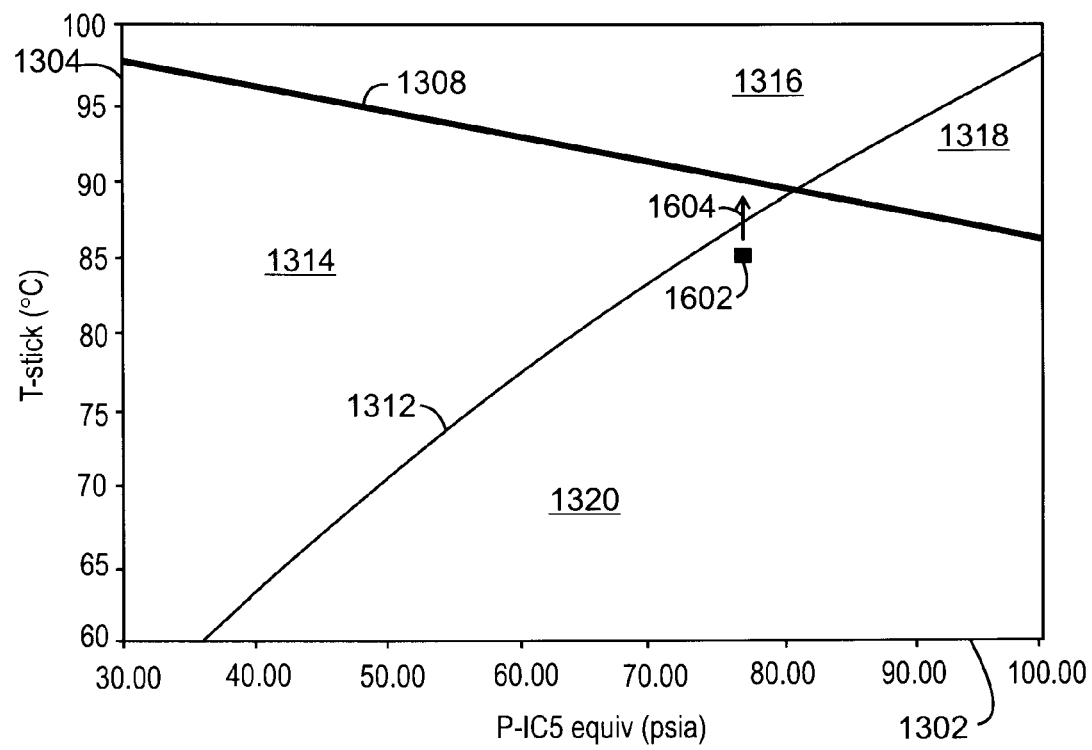
FIG. 16 is a plot of a pilot plant run showing operations in a liquid regime that led to resin sticking.
Figure 17:
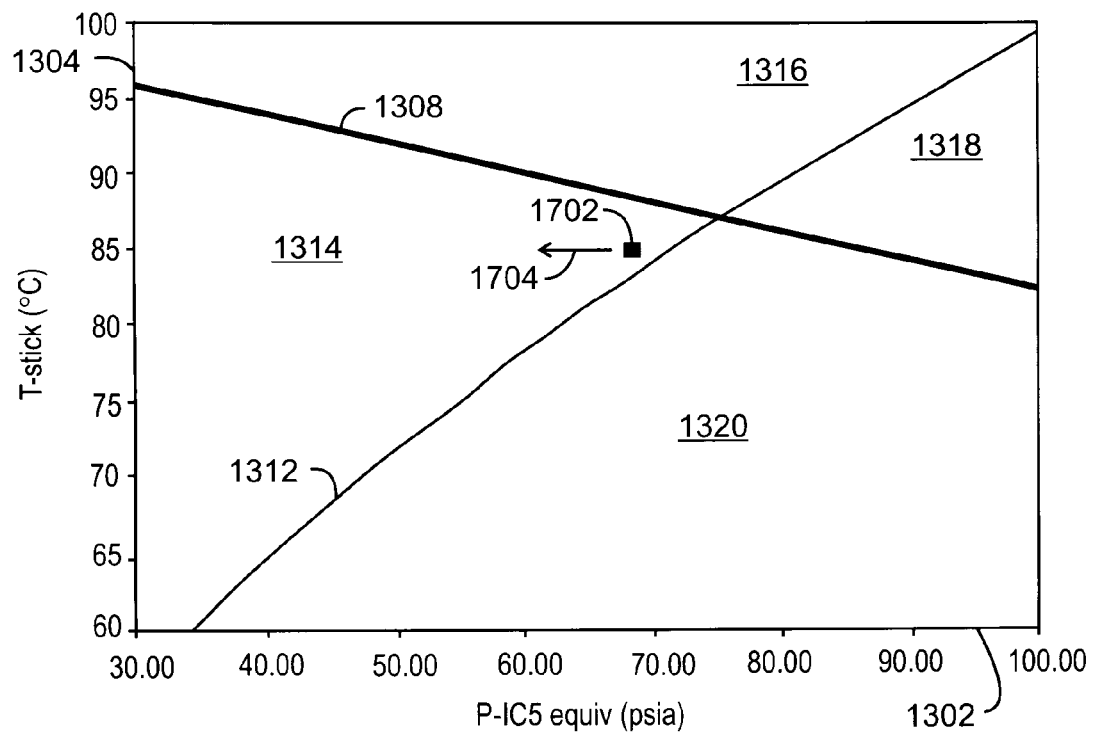
FIG. 17 is a plot of a commercial run within a safe operating window.
Figure 18:
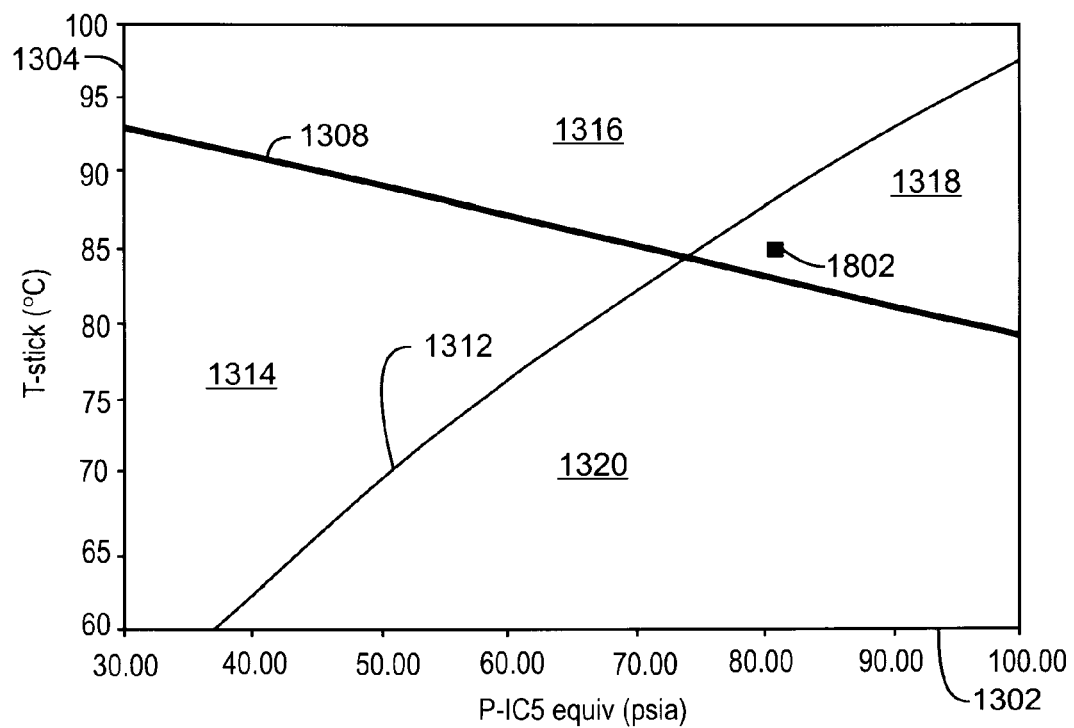
FIG. 18 is a plot of a pilot plant run performed in both a sticking and liquid regime.
Figure 19:
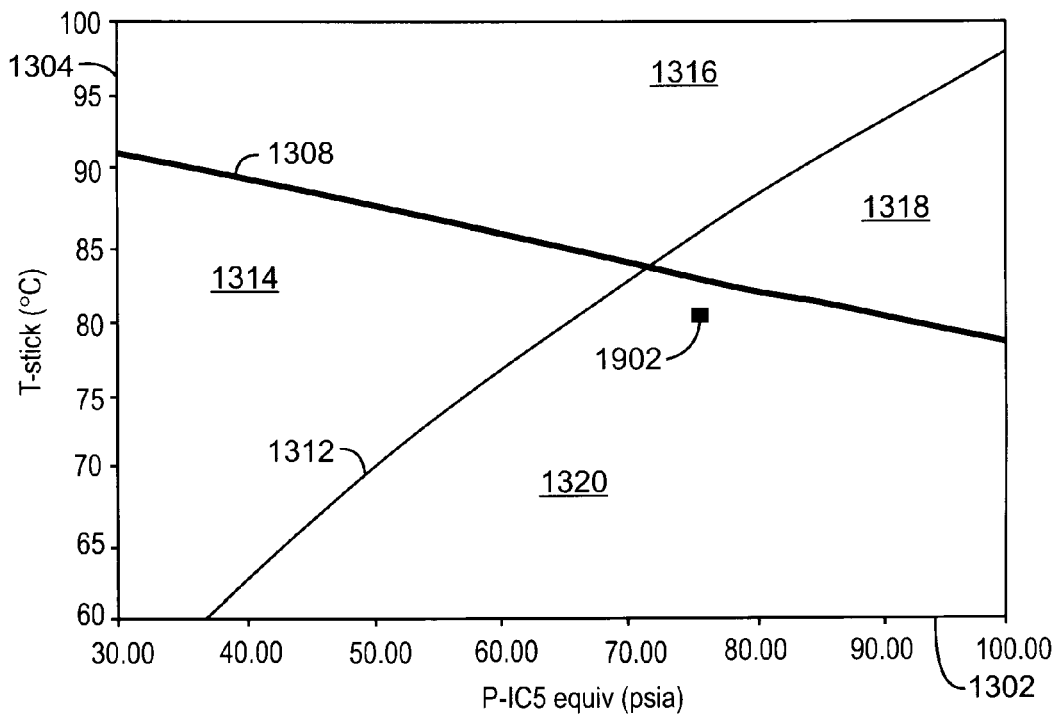
FIG. 19 is another plot of a pilot plant run performed in a liquid regime leading to resin sticking.

|  | CASE 1 FIG. 14 Catalyst 1 | CASE C1 FIG. 15 Catalyst 1 | CASE 2 FIG. 16 Catalyst 1 | CASE C2 FIG. 17 Catalyst 1 | CASE 3 FIG. 18 Catalyst 2 | CASE 4 FIG. 19 Catalyst 2 |
| --- | --- | --- | --- | --- | --- | --- |
| facility size | pilot plant | commercial | pilot plant | commercial | pilot plant | pilot plant |
| Rxn T (° C.) | 80 | 80 | 85 | 85 | 85 | 80 |
| $iC_5$ (mol %) | 17.29 | 12.1 | 18.9 | 17 | 20.3 | 18.26 |
| $iC_5$ PP, psia | 58.5 |  | 64.1 |  | 74 | 66.4 |
| Cycle Gas DP (° C.) | 72.4 |  | 75.02 |  | 77 | 74.1 |
| Density | 0.9122 | 0.9122 | 0.9195 | 0.9175 | 0.913 | 0.9174 |
| MI | 0.764 | 1 | 0.9 | 0.96 | 0.6 | 0.838 |
| MFR | 16.9 | 16.9 | 16.2 | 16.2 | 16.2 | 30.8 |

In the Catalyst 1 runs made in the pilot plant, when the $iC_5$ concentration increased beyond a certain limit, condensation occurred in the taps which made it difficult to control the bed level. In pilot plant runs made with Catalyst 2, formation of chunks, sheeting and expanded section fouling were observed above a certain $iC_5$ concentration.

FIG. 14 is a plot 1400 of a pilot plant run showing operation in a liquid regime in a first case study. Like numbered items are as described with respect to FIG. 13. The run used Catalyst 1 to produce a very low density polyethylene (VLDPE) resin, with the resin and reactor parameters described under Case 1 in Table 2. The square 1402 lies below the lower reactor limit 1312 in the liquid regime 1320 where capillary condensation is expected. The square 1402 indicates reactor operations at 17.3 mol % $iC_5$ and a reactor temperature of 80° C., above which the operation resulted in condensation in the taps and loss of control in the bed level. The operations may be recovered by lowering the $iC_5$ concentration in the reactor, as indicated by an arrow 1404, to lower the equivalent partial pressure of the $iC_5$, and shift operations back into the non-sticking regime 1314.

FIG. 15 is a plot 1500 of operations within a non-sticking regime during a commercial plant run. Like numbered items are as described with respect to FIG. 13. The plot 1500 shows the model prediction of the operability window for the commercial production of a VLDPE resin with Catalyst 1, with the resin and reactor parameters described under Case C1 in Table 2. The square 1502 indicates operations at 12.1% $iC_5$ and a reactor temperature of 80° C. The square 1502 lies within the non-sticking regime 1314, very close to the neck where the limits 1308 and 1312 meet, which means it is already near the maximum safe production limit.

FIG. 16 is a plot 1600 of a pilot plant run showing operations in a liquid regime 1320 that led to resin sticking. Like numbered items are as described with respect to FIG. 13. The plot 1600 shows the model prediction of the operability window for the pilot plant production of a metallocene linear low density polyethylene (mLLDPE) resin with Catalyst with the resin and reactor parameters described under Case 2 in Table 2. The square 1602 indicates operations at 18.9% $iC_5$ and a reactor temperature of 85° C., which was just below the lower temperature limit 1312 in the liquid regime 1320. In this area capillary condensation was expected, and, subsequently, the reactor did have condensation in the taps and a loss of control in the bed level. The operations may be recovered by raising the temperature, as indicated by an arrow 1604, to lower the condensation of the $iC_5$, and shift operations back into the non-sticking regime 1314.

FIG. 17 is a plot 1700 of a commercial run within a non-sticking regime 1314. Like numbered items are as described with respect to FIG. 13. The plot 1700 shows the model prediction of the operability window for commercial production of mLLDPE resin made with Catalyst 1 with the resin and reactor parameters described under Case C2 in Table 2. The reactor operations point, indicated by the square 1702 at 17% $iC_5$ and a reactor temperature of 85° C., was within the non-sticking regime 1314, but was close to the lower temperature limit 1312. Any increase in the $iC_5$ concentration, or decrease in temperature, may move operations into the liquid regime 1320 causing stickiness or loss of reactor control in the resin. As the reactor temperature is often determined by the requirements for MFR control, the liquid regime 1320 can be avoided by adjusting the $iC_5$ level at that temperature, as indicated by an arrow 1704.

FIG. 18 is a plot 1800 of a pilot plant run performed in both a sticking and liquid regime 1318. Like numbered items are as described with respect to FIG. 13. The plot 1800 shows the operating window for the production of VLDPE resin with Catalyst 2 with the resin and reactor parameters described under Case 3 in Table 2. The reactor operations point, indicated by the square 1802 at 20.3% $iC_5$ and a reactor temperature of 85° C., landed in the stick and liquid regime 1318 where both the resin melting and liquid condensation occur. As could be expected, operations in this regime 1318 resulted in expanded section fouling and chunks in the reactor.

FIG. 19 is another plot 1900 of a pilot plant run performed in a liquid regime 1318 leading to resin sticking. Like numbered items are as described with respect to FIG. 13. The plot 1900 shows the operating window for the production of mLLDPE resin with Catalyst 2 with the resin and reactor parameters described under Case 4 in Table 2. The reactor operations point, indicated by the square 1902 at 18.3% $iC_5$ and a reactor temperature of 80° C., resided in the liquid regime 1320 where liquid condensation occurs, causing the resin to stick. Operating at this point resulted in chunking the entire bed in the reactor.

As indicated by the examples in FIGS. 14-19, the model predicts substantially predicts the operating window both in a pilot plant reactor and in a commercial plant. The model can be used to set optimum operating conditions to maximize the production rate by increasing the $iC_5$ concentration while still remaining in the non-sticking regime 1314. Further, the model can be used to identify operations in problematic regimes 1316, 1318, and 1320, and adjust the reactor conditions before operational problems or shut-downs occur.

The methods described herein can be used in determining an empirical model to prevent sticking in a reactor. For example, the stickiness temperature varies linearly with the $iC_5$ partial pressure over a wide range of resin properties. The stickiness temperature for resins made with metallocene catalysts has been correlated to density, MI, MFR, temperature, and the equivalent partial pressure of the ICA in the reactor. The correlation was validated with bed settling tests in a pilot reactor and found to agree within ±3° C. Further, the effect of particle size on resin stickiness temperature is observed to be negligible within the experimental error for resin melting and $iC_5$ condensation. Thus, the methods described herein use the stickiness temperature correlation and dew point calculations to determine a safe operability window for polymerization processes using metallocene catalysts.

Test Conditions and Materials

In Table 1 and elsewhere herein polymer density refers to density measured in accordance with ASTM 1505 and ASTM D-1928. A plaque is made and conditioned for one hour at 100° C. to approach equilibrium crystallinity. Measurement for density is then made in a density gradient column. Throughout this disclosure, the abbreviation "MI" (or $I_2$) denotes melt index. MI is measured in accordance with ASTM D1238 (at 190° C., 2.16 kg weight). Flow index (FI or $I_{21}$) is measured in accordance with ASTM D1238 (190° C., 21.6 kg). The melt index ratio (MIR) is calculated by determining the ratio of FI to MI (FI/MI).

In Table 1 and elsewhere herein, Catalyst 1 is a metallocene catalyst that is commercially available from Univation Technologies, LLC as XCAT™ HP-100 Catalyst. Catalyst 2 is a silica supported bis(n-propyl-cyclopentadiene) hafnium dimethyl that was activated with methylalumoxane. Catalyst 3 is a metallocene catalyst that is commercially available from the Univation Technologies, LLC as XCAT™ EZ-100 Catalyst.

Reactors

The methods described herein may be used in any number of pilot plant or commercial size reactors including any number of designs. For example, the model can be used in commercial-scale reactions, such as gas-phase fluidized-bed polymerization reactions, that can be monitored and optionally also controlled in accordance with the invention. Some such reactions can occur in a reactor having the geometry of the fluidized bed reactor 102 discussed with respect to FIG. 1.

In some embodiments, a continuous gas phase fluidized bed reactor is monitored and optionally also controlled in accordance with the invention while it operates to perform polymerization. The polymerization is performed by mixing gaseous feed streams of the primary monomer and hydrogen together with liquid or gaseous comonomer, for example, in a mixing tee arrangement. The mixture can then be introduced below the reactor bed into the recycle gas line.

For example, the primary monomer may be ethylene and the comonomer may be 1-hexene. The individual flow rates of ethylene, hydrogen, and comonomer are controlled to maintain fixed gas composition targets. The ethylene concentration is controlled to maintain a constant ethylene partial pressure. The hydrogen is controlled to maintain constant hydrogen to ethylene mole ratio. The hexene is controlled to maintain a constant hexene to ethylene mole ratio (or alternatively, the flow rates of comonomer and ethylene are held at a fixed ratio). The concentration of all gases is measured by an on-line gas chromatograph to ensure relatively constant composition in the recycle gas stream. A solid or liquid catalyst is injected directly into the fluidized bed using purified nitrogen as a carrier. The feed rate of catalyst is adjusted to maintain a constant production rate.

The reactor bed, which contains the growing polymer particles, is maintained in a fluidized state by the continuous flow of makeup feed and recycle gas through the reaction zone. In some implementations, a superficial gas velocity of 1 to 3 ft/sec is used to achieve this, and the reactor is operated at a total pressure of 300 psig. To maintain a constant reactor temperature, the temperature of the recycle gas is continuously adjusted up or down to accommodate any changes in the rate of heat generation due to the polymerization. The fluidized bed is maintained at a constant height by withdrawing a portion of the bed at a rate equal to the rate of formation of particulate product.

The product is removed continuously or nearly continuously via a series of valves into a fixed volume chamber, which is simultaneously vented back to the reactor. This allows for highly efficient removal of the product, while recycling a large portion of the unreacted gases back to the reactor. The removed product is purged to remove entrained hydrocarbons and treated with a small stream of humidified nitrogen to deactivate any trace quantities of residual catalyst. In other embodiments, a reactor is monitored and optionally also controlled in accordance with the invention while it operates to perform polymerization using any of a variety of different processes (e.g., slurry, or gas phase processes).

In some embodiments, a polymerization reaction that is a continuous gas phase process (e.g., a fluid bed process) is monitored and optionally also controlled in accordance with the techniques described herein. A fluidized bed reactor for performing such a process typically comprises a reaction zone and a so-called velocity reduction zone. The reaction zone comprises a bed of growing polymer particles, formed polymer particles and a minor amount of catalyst particles fluidized by the continuous flow of the gaseous monomer and diluent to remove heat of polymerization through the reaction zone. Optionally, some of the re-circulated gases may be cooled and compressed to form liquids that increase the heat removal capacity of the circulating gas stream when readmitted to the reaction zone. This method of operation is referred to as "condensed mode." A suitable rate of gas flow may be readily determined by simple experiment. Make up of gaseous monomer to the circulating gas stream is at a rate equal to the rate at which particulate polymer product and monomer associated therewith is withdrawn from the reactor and the composition of the gas passing through the reactor is adjusted to maintain an essentially steady state gaseous composition within the reaction zone.

The gas leaving the reaction zone is passed to the velocity reduction zone where entrained particles are removed. Finer entrained particles and dust may be removed in a cyclone and/or fines filter. The gas is compressed in a compressor and passed through a heat exchanger wherein the heat of polymerization is removed, and then returned to the reaction zone.

A reaction monitored and optionally also controlled in accordance with some embodiments of the invention can produce homopolymers of olefins (e.g., homopolymers of ethylene), and/or copolymers, terpolymers, and the like, of olefins, particularly ethylene, and at least one other olefin. The olefins, for example, may contain from 2 to 16 carbon atoms in one embodiment; and in another embodiment, ethylene and a comonomer comprising from 3 to 12 carbon atoms in another embodiment; and ethylene and a comonomer comprising from 4 to 10 carbon atoms in yet another embodiment; and ethylene and a comonomer comprising from 4 to 8 carbon atoms in yet another embodiment. A reaction monitored and optionally also controlled in accordance with the invention can produce polyethylenes. Such polyethylenes can be homopolymers of ethylene and interpolymers of ethylene and at least one alpha-olefin wherein the ethylene content is at least about 50% by weight of the total monomers involved. Exemplary olefins that may be utilized in embodiments of the invention are ethylene, propylene, 1-butene, 1-pentene, 1-hexene, 1-heptene, 1-octene, 4-methylpent-1-ene, 1-decene, 1-dodecene, 1-hexadecene, and the like. Also utilizable herein are polyenes such as 1,3-hexadiene, 1,4-hexadiene, cyclopentadiene, dicyclopentadiene, 4-vinylcyclohex-1-ene, 1,5-cyclooctadiene, 5-vinylidene-2-norbornene and 5-vinyl-2-norbornene, and olefins formed in situ in the polymerization medium. As may be understood, the choice of the comonomer affects the determination of the effective partial pressure of the ICA, which can change the predicted and actual values for the stickiness temperature.

When olefins are formed in situ in the polymerization medium, the formation of polyolefins containing long chain branching may occur. In the production of polyethylene or polypropylene, comonomers may be present in the polymerization reactor. When present, the comonomer may be present at any level with the ethylene or propylene monomer that will achieve the desired weight percent incorporation of the comonomer into the finished resin. In one embodiment of polyethylene production, the comonomer is present with ethylene in a mole ratio range in the gas phase of from about 0.0001 to about 50 (comonomer to ethylene), and from about 0.0001 to about 5 in another embodiment, and from about 0.0005 to about 1.0 in yet another embodiment, and from about 0.001 to about 0.5 in yet another embodiment. Expressed in absolute terms, in making polyethylene, the amount of ethylene present in the polymerization reactor may range to up to about 1000 atmospheres pressure in one embodiment, and up to about 500 atmospheres pressure in another embodiment, and up to about 100 atmospheres pressure in yet another embodiment, and up to about 50 atmospheres in yet another embodiment, and up to about 10 atmospheres in yet another embodiment.

Hydrogen gas is often used in olefin polymerization to control the final properties of the polyolefin. For some types of catalyst systems, it is known that increasing concentrations (or partial pressures) of hydrogen may alter the molecular weight or melt index (MI) of the polyolefin generated. The MI can thus be influenced by the hydrogen concentration. The amount of hydrogen in the polymerization can be expressed as a mole ratio relative to the total polymerizable monomer, for example, ethylene, or a blend of ethylene and hexene or propylene. The amount of hydrogen used in some polymerization processes is an amount necessary to achieve the desired MI (or molecular weight) of the final polyolefin resin. In one embodiment, the mole ratio in the gas phase of hydrogen to total monomer ($H_2$ to monomer) is greater than about 0.00001. The mole ratio is greater than about 0.0005 in another embodiment, greater than about 0.001 in yet another embodiment, less than about 10 in yet another embodiment, less than about 5 in yet another embodiment, less than about 3 in yet another embodiment, and less than about 0.10 in yet another embodiment, wherein a desirable range may comprise any combination of any upper mole ratio limit with any lower mole ratio limit described herein. Expressed another way, the amount of hydrogen in the reactor at any time may range to up to about 10 ppm in one embodiment, or up to about 100 or about 3000 or about 4000 or about 5000 ppm in other embodiments, or between about 10 ppm and about 5000 ppm in yet another embodiment, or between about 500 ppm and about 2000 ppm in another embodiment.

A reactor monitored and optionally also controlled in accordance with some embodiments of the invention can be an element of a staged reactor employing two or more reactors in series, wherein one reactor may produce, for example, a high molecular weight component and another reactor may produce a low molecular weight component.

A reactor monitored and optionally also controlled in accordance with the invention can implement a slurry or gas phase process in the presence of a bulky ligand metallocene-type catalyst system and in the absence of, or essentially free of, any scavengers, such as triethylaluminum, trimethylaluminum, tri-isobutylaluminum and tri-n-hexylaluminum and diethyl aluminum chloride, dibutyl zinc and the like. By "essentially free," it is meant that these compounds are not deliberately added to the reactor or any reactor components, and if present, are present in less than about 1 ppm in the reactor.

A reactor monitored and optionally also controlled in accordance with the invention can employ one or more catalysts combined with up to about 10 wt % of a metal-fatty acid compound, such as, for example, an aluminum stearate, based upon the weight of the catalyst system (or its components). Other metals that may be suitable include other Group 2 and Group 5-13 metals. In other embodiments, a solution of the metal-fatty acid compound is fed into the reactor. In other embodiments, the metal-fatty acid compound is mixed with the catalyst and fed into the reactor separately. These agents may be mixed with the catalyst or may be fed into the reactor in a solution, slurry, or as a solid (preferably as a powder) with or without the catalyst system or its components.

In a reactor monitored and optionally also controlled in accordance with some embodiments of the invention, supported catalyst(s) can be combined with activators and can be combined by tumbling and/or other suitable means, with up to about 2.5 wt % (by weight of the catalyst composition) of an antistatic agent, such as an ethoxylated or methoxylated amine, an example of which is KEMAMINE AS-990, available from ICI Specialties. Other antistatic compositions include the OCTASTAT family of compounds, more specifically Octastat 2000, 3000, and 5000.

Metal fatty acids and antistatic agents can be added as solid slurries, solutions, or solids (preferably as a powder) as separate feeds into the reactor. One advantage of this method of addition is that it permits on-line adjustment of the level of the additive.

Examples of polymers that can be produced in accordance with the invention include the following: homopolymers and copolymers of $C_2$-$C_{18}$ alpha olefins; polyvinyl chlorides, ethylene propylene rubbers (EPRs); ethylene-propylene diene rubbers (EPDMs); polyisoprene; polystyrene; polybutadiene; polymers of butadiene copolymerized with styrene; polymers of butadiene copolymerized with isoprene; polymers of butadiene with acrylonitrile; polymers of isobutylene copolymerized with isoprene; ethylene butene rubbers and ethylene butene diene rubbers; and polychloroprene; norbornene homopolymers and copolymers with one or more $C_2$-$C_{18}$ alpha olefin; terpolymers of one or more $C_2$-$C_{18}$ alpha olefins with a diene.

Monomers that can be present in a reactor monitored and optionally also controlled in accordance with the invention include one or more of: $C_2$-$C_{18}$ alpha olefins such as ethylene, propylene, and optionally at least one diene, for example, hexadiene, dicyclopentadiene, octadiene including methyloctadiene (e.g., 1-methyl-1,6-octadiene and 7-methyl-1,6-octadiene), norbornadiene, and ethylidene norbornene; and readily condensable monomers, for example, isoprene, styrene, butadiene, isobutylene, chloroprene, acrylonitrile, cyclic olefins such as norbornenes.

Fluidized bed polymerization can be monitored and optionally also controlled in accordance with some embodiments of the invention. The reaction can be any type of fluidized polymerization reaction and can be carried out in a single reactor or multiple reactors such as two or more reactors in series.

In various embodiments, any of many different types of polymerization catalysts can be used in a polymerization process monitored and optionally also controlled in accordance with the present invention. A single catalyst may be used, or a mixture of catalysts may be employed, if desired. The catalyst can be soluble or insoluble, supported or unsupported. It may be a prepolymer, spray dried with or without a filler, a liquid, or a solution, slurry/suspension, or dispersion. These catalysts are used with cocatalysts and promoters well known in the art. Typically these are alkylaluminums, alkylaluminum halides, alkylaluminum hydrides, as well as aluminoxanes. For illustrative purposes only, examples of suitable catalysts include Ziegler Natta catalysts, chromium based catalysts, vanadium based catalysts (e.g., vanadium oxychloride and vanadium acetylacetonate), metallocene catalysts and other single-site or single-site-like catalysts, cationic forms of metal halides (e.g., aluminum trihalides), anionic initiators (e.g., butyl lithiums), cobalt catalysts and mixtures thereof, Nickel catalysts and mixtures thereof, rare earth metal catalysts (i.e., those containing a metal having an atomic number in the Periodic Table of 57 to 103), such as compounds of cerium, lanthanum, praseodymium, gadolinium and neodymium.

The catalyst may comprise a metallocene. Metallocenes as described herein include "half sandwich" and "full sandwich" compounds having one or more Cp ligands (cyclopentadienyl and ligands isolobal to cyclopentadienyl) bound to at least one Group 3 to Group 12 metal atom, and one or more leaving groups bound to the at least one metal atom.

Hereinafter, these compounds will be referred to as "metallocenes" or "metallocene catalyst components." The metallocene catalyst component may be supported on a support material, and may be supported with or without another catalyst component. In one embodiment, the one or more metallocene catalyst components are represented by the formula (I):

$$Cp^A Cp^B MX_n \tag{I}$$

wherein M is a metal atom selected from the group consisting of Groups 3 through 12 atoms and lanthanide Group atoms in one embodiment. For example, M may be selected from Ti, Zr, Hf atoms. Each leaving group X is chemically bonded to M; each Cp group is chemically bonded to M; and n is 0 or an integer from 1 to 4, and may be either 1 or 2 in a particular embodiment.

The Cp ligands are one or more rings or ring systems, at least a portion of which includes π-bonded systems, such as cycloalkadienyl ligands and heterocyclic analogues. The Cp ligands are distinct from the leaving groups bound to the catalyst compound in that they are not highly susceptible to substitution or abstraction reactions. The ligands represented by $Cp^A$ and $Cp^B$ in formula (I) may be the same or different cyclopentadienyl ligands or ligands isolobal to cyclopentadienyl, either or both of which may contain heteroatoms and either or both of which may be substituted by at least one R group. Non-limiting examples of substituent R groups include groups selected from hydrogen radicals, alkyls, alkenyls, alkynyls, cycloalkyls, aryls, acyls, aroyls, alkoxys, aryloxys, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof. In one embodiment, $Cp^A$ and $Cp^B$ are independently selected from the group consisting of cyclopentadienyl, indenyl, tetrahydroindenyl, fluorenyl, and substituted derivatives of each. (As used herein, the term "substituted" means that the group following that term possesses at least one moiety in place of one or more hydrogens in any position, which moieties are selected from such groups as halogen radicals (e.g., Cl, F, Br), hydroxyl groups, carbonyl groups, carboxyl groups, amine groups, phosphine groups, alkoxy groups, phenyl groups, naphthyl groups, $C_1$ to $C_{10}$ alkyl groups, $C_2$ to $C_{10}$ alkenyl groups, and combinations thereof. Examples of substituted alkyls and aryls include, but are not limited to, acyl radicals, alkylamino radicals, alkoxy radicals, aryloxy radicals, alkylthio radicals, dialkylamino radicals, alkoxycarbonyl radicals, aryloxycarbonyl radicals, carbomoyl radicals, alkyl- and dialkyl-carbamoyl radicals, acyloxy radicals, acylamino radicals, arylamino radicals, and combinations thereof).

In one embodiment, each leaving group X in the formula (I) above may be independently selected from the group consisting of halogen ions, hydrides, $C_{1-12}$ alkyls, $C_{2-12}$ alkenyls, $C_{6-12}$ aryls, $C_{7-20}$ alkylaryls, $C_{1-12}$ alkoxys, $C_{6-16}$ aryloxys, $C_{7-18}$ alkylaryloxys, $C_{1-12}$ fluoroalkyls, $C_{6-12}$ fluoroaryls, and $C_{1-12}$ heteroatom-containing hydrocarbons, and substituted derivatives thereof. As used herein, the phrase "leaving group" refers to one or more chemical moieties bound to the metal center of the catalyst component, which can be abstracted from the catalyst component by an activator, thus producing a species active towards olefin polymerization or oligomerization.

The structure of the metallocene catalyst component may take on many forms, such as those disclosed in, for example, U.S. Pat. Nos. 5,026,798, 5,703,187, and 5,747,406, including a dimer or oligomeric structure, such as disclosed in, for example, U.S. Pat. Nos. 5,026,798 and 6,069,213. Others include those catalysts described in U.S. Patent Application Publication Nos. US2005/0124487A1, US2005/0164875A1, and US2005/0148744. In other embodiments, the metallocene may be formed with a hafnium metal atom, such as is described in U.S. Pat. No. 6,242,545.

In certain embodiments, the metallocene catalysts components described above may include their structural or optical or enantiomeric isomers (racemic mixture), and, in one embodiment, may be a pure enantiomer.

In various embodiments, a polymerization reaction monitored and optionally also controlled in accordance with the invention can employ other additives, such as (for example) inert particulate particles.

It should be understood that while some embodiments of the present invention are illustrated and described herein, the invention is not to be limited to the specific embodiments described and shown. The phrases, unless otherwise specified, "consists essentially of" and "consisting essentially of" do not exclude the presence of other steps, elements, or materials, whether or not, specifically mentioned in this specification, as long as such steps, elements, or materials, do not affect the basic and novel characteristics of the invention, additionally, they do not exclude impurities normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

As used herein, "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

All numerical values are "about" or "approximately" the indicated value, and take into account experimental error and variations that would be expected by a person having ordinary skill in the art. Further, various terms have been defined above. To the extent a term used in a claim is not defined above, it should be given the broadest definition persons in the pertinent art have given that term as reflected in at least one printed publication or issued patent. All patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention can be devised without departing from the basic scope thereof, and the scope thereof is determined by the claims that follow.

What is claimed is:

1. A method of modeling a stickiness temperature for a resin, wherein the resin is made in the presence of at least one catalyst, the method comprising:
    measuring a stickiness temperature of a resin at each of a plurality of concentrations of induced condensing agent (ICA) in a testing device;
    measuring a density, a melt index (MI), and a high load melt index (HLMI) for the resin;
    calculating a melt flow ratio (MFR) by dividing the HLMI by the MI;
    calculating an equivalent partial pressure $((P_{ICA})_{equiv})$ of the ICA by accounting for the partial pressure of isomers that accumulate in a reactor;
    determining an equation that relates the stickiness temperature to the $((P_{ICA})_{equiv})$, based, at least in part, on the density, the MI, and the MFR of the resin.

2. The method of claim 1, comprising:
    repeating the testing for a number of resins made with said at least one catalyst using a plurality of conditions to generate a more extensive data set; and
    generating the equation using the more extensive data set.

3. The method of claim 1, wherein said at least one catalyst is selected from the group consisting of metallocenes, Ziegler-Natta, chromium, chromium oxide, $AlCl_3$, cobalt, iron, palladium, and any combinations thereof.

4. The method of claim 1, wherein the determining an equation that relates the stickiness temperature to the $((P_{ICA})_{equiv})$ comprises performing a least squares analysis.

5. A method of controlling a polymerization reaction to remain in a non-sticking regime, comprising:
    measuring parameters for the polymerization reaction including a reactor temperature and a concentration of an induced condensing agent (ICA) in a polymerization reactor;
    calculating an equivalent partial pressure $((P_{ICA})_{equiv})$ of the ICA;
    locating the polymerization reaction in a two dimension space defined by a reactor temperature dimension and a $(P_{ICA})_{equiv}$ dimension;
    comparing the location in the two dimensional space to an non-sticking regime defined as the space between an upper temperature limit (UTL) curve and a lower temperature limit (LTL) curve; and
    adjusting the parameters of the polymerization reaction to keep the polymerization reaction within the non-sticking regime.

6. The method of claim 5, wherein the ICA is selected from the group consisting of hexane, isohexane, pentane, isopentane, butane, isobutane, and any combinations thereof.

7. The method of claim 5, wherein the ICA is isopentane.

8. The method of claim 5, wherein calculating the $(P_{ICA})_{equiv}$ of the ICA comprises:
    measuring the concentration of the ICA in the reactor;
    measuring an amount of other condensable components in the reactor;
    calculating the partial pressure of the ICA $(P_{ICA})$ in the reactor; and
    adjusting the $P_{ICA}$ account for the amount of other condensable components, resulting in the $(P_{ICA})_{equiv}$.

9. The method of claim 8, wherein the other condensable components comprise isomers of a comonomer.

10. The method of claim 5, comprising measuring physical properties of a plurality of resins generated by a catalyst system, wherein the physical properties include a melt index (MI) of each resin, a density of each resin, and a melt flow ratio of each resin.

11. The method of claim 10 wherein the catalyst system comprises at least one catalyst selected from the group consisting of metallocenes, Ziegler-Natta, chromium, chromium oxide, $AlCl_3$, cobalt, iron, palladium, and any combinations thereof.

12. The method of claim 10, comprising:
    generating a model of stickiness temperature $(T_{stick})$ based on an equivalent partial pressure $((P_{ICA})_{equiv})$ of an induced condensing agent (ICA), wherein the model generates a predicted $T_{stick}$ value at each of a plurality of values of the $(P_{ICA})_{equiv}$ of the ICA, based at least in part on the melt index (MI) of the resin, the density of the resin, and a melt flow ratio for the resin;
    generating the UTL curve by subtracting an upper temperature delta from each value predicted for $T_{stick}$;
    generating a dew point curve for the ICA that predicts a dew point at each of the plurality of values of the $(P_{ICA})_{equiv}$ of the ICA; and
    generating the LTL curve by adding a lower temperature delta to each value predicted for the dew point.

13. The method of claim 12, comprising setting the upper temperature delta to at least about five degrees Celsius.

14. The method of claim 12, comprising setting the lower temperature delta to compensate for capillary condensation in a fluidized bed.

15. The method of claim 12, comprising setting the lower temperature delta to at least about ten degrees Celsius.

16. The method of claim 5, comprising reducing the reactor temperature to move the polymerization reaction into the non-sticking regime.

17. The method of claim 5, comprising raising the reactor temperature to move the polymerization reaction into the non-sticking regime.

18. The method of claim 5, comprising reducing the amount of recirculated ICA to reduce the $(P_{ICA})_{equiv}$ and move the polymerization reaction into the non-sticking regime.

19. The method of claim 5, comprising raising the reactor temperature and raising the ICA concentration to increase productivity, while not allowing the polymerization reactor to leave the non-sticking regime.

* * * * *